US012753405B2

(12) United States Patent
Oberstrass et al.

(10) Patent No.: US 12,753,405 B2
(45) Date of Patent: Oct. 6, 2026

(54) METHODS FOR PREPARING A LIBRARY OF POLYNUCLEOTIDE MOLECULES

(71) Applicant: ULTIMA GENOMICS, INC., Fremont, CA (US)

(72) Inventors: Florian Oberstrass, Mento Park, CA (US); Daniel Mazur, San Diego, CA (US)

(73) Assignee: Ultima Genomics, Inc., Fremont, CA (US)

( * ) Notice: Subject to any disclaimer, the term of this patent is extended or adjusted under 35 U.S.C. 154(b) by 1026 days.

(21) Appl. No.: 17/773,835

(22) PCT Filed: Nov. 5, 2020

(86) PCT No.: PCT/IB2020/060420

§ 371 (c)(1),
(2) Date: May 2, 2022

(87) PCT Pub. No.: WO2021/090231

PCT Pub. Date: May 14, 2021

(65) Prior Publication Data

US 2022/0372472 A1 Nov. 24, 2022

Related U.S. Application Data

(63) Continuation of application No. PCT/US2020/017491, filed on Feb. 10, 2020.

(60) Provisional application No. 62/930,921, filed on Nov. 5, 2019, provisional application No. 63/033,344, filed on Jun. 2, 2020.

(51) Int. Cl.

| | |
|---|---|
| ***C12N 15/10*** | (2006.01) |
| ***C12P 19/34*** | (2006.01) |
| ***C40B 40/06*** | (2006.01) |

(52) U.S. Cl.

CPC .......... *C12N 15/1093* (2013.01); *C12P 19/34* (2013.01); *C40B 40/06* (2013.01)

(58) Field of Classification Search

None

See application file for complete search history.

(56) References Cited

U.S. PATENT DOCUMENTS

| | | | |
|---|---|---|---|
| 8,765,380 | B2 | 7/2014 | Berka et al. |
| 8,772,473 | B2 | 7/2014 | Huang et al. |
| 9,902,951 | B2 | 2/2018 | Kawashima et al. |
| 2010/0279295 | A1 | 11/2010 | Roy et al. |
| 2011/0236891 | A1 | 9/2011 | Li et al. |
| 2015/0225775 | A1 | 8/2015 | Satya |
| 2016/0090623 | A1 | 3/2016 | Rigatti et al. |
| 2017/0226567 | A1 | 8/2017 | Xiao et al. |
| 2017/0240886 | A1 | 8/2017 | Oleinikov |

FOREIGN PATENT DOCUMENTS

| | | | | |
|---|---|---|---|---|
| WO | WO 2005090599 | A2 | 9/2005 | |
| WO | 2016058136 | A1 | 4/2016 | |
| WO | 2018140695 | A1 | 8/2018 | |
| WO | WO 2019079653 | A1 | 4/2019 | |
| WO | WO-2019094651 | A1 * | 5/2019 | .......... C12Q 1/6806 |
| WO | WO 2019156983 | A1 | 8/2019 | |
| WO | WO 2020167656 | A1 | 8/2020 | |
| WO | WO 2021155371 | A1 | 8/2021 | |
| WO | 2015134552 | A1 | 9/2025 | |

OTHER PUBLICATIONS

International Search Report, mailed Jul. 14, 2021, for International Application No. PCT/IB2020/060420, 11 pages.

* cited by examiner

*Primary Examiner* — Heather Calamita
*Assistant Examiner* — Jessica D Parisi
(74) *Attorney, Agent, or Firm* — Fox Rothschild LLP

(57) ABSTRACT

The present invention relates to a method for generating a library of different polynucleotide molecules, by ligating a double-stranded polynucleotide to a plurality of different target polynucleotide duplexes, the double-stranded polynucleotide comprising: (a) a first strand comprising an annealed portion and an overhang portion; and (b) a second strand consisting essentially of an annealed portion, wherein the second strand is complementary to and annealed to the annealed portion of the first strand.

20 Claims, 18 Drawing Sheets

Specification includes a Sequence Listing.

SEQUENCE LISTING

```
<160> NUMBER OF SEQ ID NOS: 2

<210> SEQ ID NO 1
<211> LENGTH: 27
<212> TYPE: DNA
<213> ORGANISM: Artificial Sequence
<220> FEATURE:
<223> OTHER INFORMATION: Adapter

<400> SEQUENCE: 1

ggtcgcugtc accugctgcu gatttcu                                         27


<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2

uccauctcau ccctgcgtgt ctccga                                          26
```

METHODS FOR PREPARING A LIBRARY OF POLYNUCLEOTIDE MOLECULES

CROSS REFERENCE TO RELATED APPLICATIONS

This application claims the benefit of priority of International Patent Application No. PCT/US2020/017491 filed Feb. 10, 2020, U.S. Provisional Patent Application No. 63/033,344, filed Jun. 2, 2020, and U.S. Provisional Patent Application No. 62/930,921, filed Nov. 5, 2019, the contents of which are all incorporated herein by reference in their entirety.

REFERENCE TO A SEQUENCE LISTING

This application contains a sequence listing, which is submitted electronically via EFS-Web as an ASCII formatted sequence listing with a file name "368893.40420_ST25v2" and a creation date of Jan. 23, 2026, and having a size of 794 bytes. The sequence listing submitted via EFS-Web is part of the specification and is herein incorporated by reference in its entirety.

FIELD OF INVENTION

The present invention is in the field of molecular biology and relates to methods for preparing a library of polynucleotides, such as for templates to be used in subsequent enzymatic reactions.

BACKGROUND

For the amplification of a pool of different polynucleotides having unknown or partially unknown sequences, the preparation of a polynucleotide library takes place, which requires the addition of known and specific sequences that flank each of the polynucleotides of the pool. For instance, genomic DNA initially has to be sheared, after which oligonucleotide adapters are added to the ends of the fragments in order to enable their amplification, possibly by ligation. However, this step results in approximately 50% material loss, as about half of the ligated material is nonfunctional for subsequent polymerase amplification. This outcome is particularly problematic and undesired where the starting material is of minute amounts, for example, cell free DNA. Improved methods for generating uniformly labeled libraries, particularly from small starting pools of precious DNA, are greatly needed.

SUMMARY

The present invention is based, in part, on the finding that a uniformly labeled library of different polynucleotides can be obtained by performing the method disclosed herein using the molecule of the invention. The state of the art discloses the addition of an exogenous nucleic acid sequence to a plurality of different target polynucleotide duplexes by a ligation step so as to provide a library of templates for subsequent enzymatic reaction. In contrast, the herein disclosed method comprises ligating the polynucleotide of the invention to the plurality of different target polynucleotide duplexes, followed by denaturing the ligation products, annealing an oligonucleotide complementary to the polynucleotide of the invention, and extending all of the resulting free 3'-ends, thereby providing a library comprising target DNA with distinct adapters attached to each end.

According to a first aspect, there is provided a polynucleotide, comprising:

a. a first strand comprising a first annealed portion and an overhang portion wherein the overhang portion comprises at least 9 nucleotides; and b. a second strand comprising a second annealed portion, wherein the second strand is complementary to and annealed to the annealed portion of the first strand;

and wherein the first or second strand comprises at least one cleavable or excisable base.

According to another aspect, there is provided a composition comprising: (a) the polynucleotide of the invention, and (b) a solitary purine and a solitary pyrimidine, a DNA ligase, a RNA ligase, a DNA polymerase, a RNA polymerase, a cleaving agent or any combination thereof.

According to another aspect, there is provided a method for preparing a chimeric DNA molecule, comprising ligating the polynucleotide of the invention to both ends of a target double stranded DNA molecule, thereby providing a chimeric DNA molecule.

According to another aspect, there is provided a kit comprising:

a. the polynucleotide of the invention; and b. a DNA oligonucleotide comprising a nucleic acid sequence complementary to the first annealed portion or the second annealed portion of the polynucleotide of the invention.

According to another aspect, there is provided a method for generating a library of different polynucleotide molecules, the method comprising:

a. providing a plurality of different target double-stranded polynucleotides;

b. providing polynucleotide adapters, wherein each polynucleotide adapter comprises:

i. a double-stranded annealed region comprising complementarity between a first strand and a second strand and wherein the second strand consists essentially of the region of complementarity; and ii. an overhang portion on the first strand of the polynucleotide adapter;

c. ligating the double-stranded annealed regions of the polynucleotide adapters to both ends of the different target double-stranded polynucleotides to form adapter-target constructs;

d. denaturing the adapter-target constructs;

e. annealing an oligonucleotide to the second strand region of complementarity of the denatured adapter-target constructs; and f. extending the annealed oligonucleotide to produce extension products complementary to the adapter-target constructs;

thereby generating a library of different polynucleotide molecules.

According to another aspect, there is provided a method for generating a library of different polynucleotide molecules, the method comprising:

a. providing a plurality of different target double-stranded polynucleotides;

b. providing polynucleotide adapters, wherein each adapter comprises:

i. a double-stranded annealed region comprising complementarity between a first and second strand and wherein the second strand consists essentially of the region of complementarity and comprises a plurality of cleavable or excisable bases; and ii. a 5' overhang region on the first strand of the adapter;

c. ligating the polynucleotide adapters to both ends of the different target double-stranded polynucleotides to form adapter-target constructs;
d. subjecting the adapter-target constructs to conditions sufficient to cleave or excise the cleavable or excisable bases, thereby dissociating the second strand of the adapters from the first strand of the adapters; and
e. annealing an oligonucleotide to the first strand region of complementarity of the adapter-target constructs;

thereby generating a library of different polynucleotide molecules.

According to another aspect, there is provided a method for generating a library of different polynucleotide molecules, the method comprising:

a. providing a plurality of different target double-stranded polynucleotides;
b. providing polynucleotide adapters, wherein each adapter comprises:
    i. a double-stranded annealed region comprising complementarity between a first and second strand and wherein the second strand consists essentially of the region of complementarity and comprises a plurality of cleavable or excisable bases; and
    ii. a 5' overhang region on the first strand of the adapter;
c. ligating the polynucleotide adapters to both ends of the different target double-stranded polynucleotides to form adapter-target constructs;
d. subjecting the adapter-target constructs to conditions sufficient to cleave or excise the cleavable or excisable bases, thereby dissociating the second strand of the adapters from the first strand of the adapters; and
e. annealing an oligonucleotide to the first strand region of complementarity of the adapter-target constructs;

thereby generating a library of different polynucleotide molecules.

According to some embodiments, the first annealed portion and the second strand comprise the same number of nucleotides.

According to some embodiments, the polynucleotide is DNA, RNA or a mixture of DNA and RNA.

According to some embodiments, the overhang portion is a 5'-end overhang of the first strand.

According to some embodiments, the overhang portion is a 3'-end overhang of the first strand.

According to some embodiments, the first strand further comprises a single base second overhang at an end opposite to an end with the overhang portion.

According to some embodiments, the single base overhang is a thymine base (T) overhang.

According to some embodiments, a first nucleotide at the 5'-end of the first strand, the second strand, or both lacks a free phosphate group.

According to some embodiments, the overhang portion is a 5'-end overhang, and the first nucleotide at the 3'-end of the second strand is a blocked nucleotide, optionally wherein the blocked nucleotide is a dideoxynucleotide or a 3' hexanediol modified nucleotide.

According to some embodiments, the first annealed portion, the second annealed portion, or both comprises a barcode nucleotide sequence, a sequence complementary of the barcode nucleotide sequence, a portion of the barcode nucleotide sequence, or a portion of the sequence complementary of the barcode sequence.

According to some embodiments, the first strand comprises the barcode nucleotide sequence, and the barcode nucleotide sequence extends from the annealed portion into the overhang portion.

According to some embodiments, the overhang region comprises a sequence complementary to a 3' region of a universal primer.

According to some embodiments, the cleavable or excisable base is selected from a ribonucleic acid (RNA) base, a uracil base, an inosine base, 2,6-diamino-4-hydroxy-5-formamidopyrimidine (FapyG) base, 8-oxo-7,8-dihydroguanine (8oxoG) base, and a photocleavable base.

According to some embodiments, the polynucleotide comprises deoxyribonucleic acid (DNA) and the cleavable or excisable base is an RNA bases, and wherein the nucleic acid molecule is devoid of RNA bases other than the cleavable or excisable base.

According to some embodiments, the at least one cleavable or excisable base is proximal to a 5' end, proximal to a 3' end or both.

According to some embodiments, the at least one cleavable or excisable is within 7 bases of either end.

According to some embodiments, the first or second strand comprises a plurality of cleavable or excisable bases.

According to some embodiments, a first cleavable or excisable base of the plurality of cleavable or excisable bases is sufficiently close to a second cleavable or excisable base such that excision of the first cleavable base and the second cleavable base induces dissociation from a complementary strand of an intervening base, optionally wherein excision of the first cleavable base and the second cleavable base induces dissociation from a complementary strand of all intervening base.

According to some embodiments, the first cleavable or excisable base of the plurality of cleavable or excisable bases is within 10 nucleotides to the second cleavable or excisable base.

According to some embodiments, the overhang portion or the second strand is devoid of a stretch of more than 9 bases that is devoid of a cleavable or excisable base.

According to some embodiments, the second strand comprises a sufficient number of cleavable or excisable bases, sufficiently close to each other, such that excision of the cleavable or excisable bases induces dissociation of the second strand from the first strand.

According to some embodiments, the overhang portion of the first strand comprises a sufficient number of cleavable or excisable bases, sufficiently close to each other, such that excision of the cleavable or excisable bases induces dissociation of the first strand overhang from a complementary strand.

According to some embodiments, the second strand comprises 16 or fewer bases.

According to some embodiments, the first strand comprises a 5' overhang of at least 9 nucleotides and optionally a 3' overhang of a T base, and wherein:

a. the second strand comprises a plurality of cleavable or excisable bases and is devoid of a stretch of non-cleavable or excisable bases of sufficient length that excision of the plurality of cleavable or excisable bases does not induce dissociation of the stretch from the first strand; or
b. the first strand 5' overhang comprises at least one cleavable or excisable base.

According to some embodiments, the second strand comprises a 5' free hydroxy (OH) group.

According to some embodiments, the first strand and second strand do not both contain a cleavable or excisable base, or wherein the first strand comprises a first cleavable or excisable base and the second strand comprises a second cleavable or excisable base and the first and second cleavable or excisable bases are cleaved or excised under different conditions.

According to some embodiments, the ends are blunt ends or single base overhang ends.

According to some embodiments, a 3' end of the first strand is ligated to a 5' end of the double stranded DNA molecule.

According to some embodiments, the kit further comprises: a solitary purine and a solitary pyrimidine, a DNA ligase, an RNA ligase, a DNA polymerase, an RNA polymerase, a cleaving agent, or any combination thereof.

According to some embodiments, the nucleic acid sequence is complementary to the second annealed portion.

According to some embodiments, the DNA oligonucleotide comprises a 5' region that is not complementary to the polynucleotide and a 3' region that is complementary to the first annealed portion or the second annealed portion of the polynucleotide.

According to some embodiments, the oligonucleotide is linked to a capture moiety, optionally wherein the oligonucleotide is linked at a 5' end.

According to some embodiments, the 5' region comprises at least one cleavable or excisable base, optionally wherein the 5' region comprises a plurality of cleavable or excisable bases.

According to some embodiments, the capture moiety is 5' to the at least one cleavable or excisable base.

According to some embodiments, the kit further comprises a capturing molecule.

According to some embodiments, the polynucleotide adapters are a polynucleotide of the invention.

According to some embodiments, the target double-stranded polynucleotides are selected from the group consisting of genomic DNA or a fragment thereof, cell-free DNA, and cDNA.

According to some embodiments, the target double-stranded polynucleotides are a plurality of target DNA molecules having different sequences.

According to some embodiments, the method produces 2 copies of a target double-stranded polynucleotide in the plurality of different target double-stranded polynucleotides.

According to some embodiments, the oligonucleotide comprises a 5' end that is not complementary to the second strand region of complementarity and the extending further comprises extending from a 3' end of the adapter-target constructs to generate a 3' region complementary to the non-complementary 5' end of the oligonucleotide.

According to some embodiments, the oligonucleotide is attached to a solid support.

According to some embodiments, the non-complementary 5' end of the oligonucleotide comprises a sufficient number of cleavable bases, sufficiently close to each other, such that excision of the cleavable bases induces dissociation of the non-complementary 5' end from a complementary strand and the method further comprises g. subjecting the library of different polynucleotide molecules to conditions sufficient to cleave or excise the cleavable or excisable bases, thereby dissociating the non-complementary 5' end from a second strand to produce a single-strand overhang library;

h. contacting the single-strand overhang library with a plurality of enrichment solid supports under conditions sufficient for hybridization of a first primer of the solid supports to a single-strand overhang of a polynucleotide of the library, wherein the enrichment solid support comprises a first primer comprising a 3' region identical or homologous to a portion of the non-complementary 5' end of the oligonucleotide; and i. isolating the enrichment solid supports.

According to some embodiments, the overhang portion of the first strand comprises a sufficient number of cleavable bases, sufficiently close to each other, such that excision of the cleavable bases induces dissociation of the first strand overhang from a complementary strand and the method further comprises g. subjecting the generated library of different polynucleotide molecules to conditions sufficient to cleave or excise the cleavable or excisable bases, thereby dissociating the first strand overhang region from a complementary strand to produce a single-strand overhang library;

h. contacting the single-strand overhang library with a plurality of enrichment solid supports under conditions sufficient for hybridization of a first primer of the solid supports to a single-strand overhang of a polynucleotide of the library, wherein the enrichment solid support comprises a first primer comprising a 3' region identical or homologous to a portion of the overhang region of the first strand; and i. isolating the enrichment solid supports.

According to some embodiments, the method further comprises sealing a nick between the first primer and a strand of the polynucleotide of the single-strand overhang library, optionally wherein the sealing comprises contacting a ligase.

According to some embodiments, the isolating comprises isolating enrichment solid supports comprising a polynucleotide of the single-strand overhang library.

According to some embodiments, the oligonucleotide comprises a capture moiety, and the method further comprises contacting the library with a capturing molecule under conditions sufficient for binding of the capturing molecule to the capture moiety and isolating the capturing molecule.

According to some embodiments, the oligonucleotide comprises a capture moiety 5' to at least one cleavable or excisable base, wherein the cleavable or excisable base in the oligonucleotide is cleaved or excised by different conditions than the cleavable or excisable bases in the overhang portion the first strand, and wherein excision of the cleavable bases from the oligonucleotide induces removal of the capture moiety from the polynucleotide of the library.

According to some embodiments, the isolating comprises:

i. contacting the single-strand overhang library and enrichment solid supports with the capturing molecule under conditions sufficient for binding of the capturing molecule to the capture moiety;

ii. isolating the capturing molecule; and iii. subjecting the isolated capturing molecule to conditions sufficient to cleave or excise the cleavable or excisable bases of the oligonucleotide, thereby dissociating the enrichment solid supports linked to a library polynucleotide from the capturing molecule.

According to some embodiments, the capturing molecule is comprised on a magnetic bead and isolating the capturing molecule comprises applying a magnetic field.

According to some embodiments, the conditions sufficient to cleave or excise comprise contact with a cleaving agent configured to cleave or excise the cleavable or excisable bases.

According to some embodiments, the cleaving agent is selected from the group consisting of uracil DNA glycosylase (UDG), apyrimidinic/apurinic endonuclease (APE), endonucleases (e.g., endonuclease VIII (EndoVIII) or V (EndoV)), uracil-specific excision reagent (USER™) enzyme (a mixture of UDG and endonuclease VIII), formamidopyrimidine DNA glycosylase (Fpg), 8-oxoguanine glycosylase (OGG1), RNase (e.g., RNaseH, such as RNaseHII), ultraviolet light, and a combination thereof.

According to some embodiments, the ligating comprises ligating a 3' end of the first strand of the polynucleotide adapters to both ends of the different target double-stranded polynucleotides.

According to some embodiments, the conditions in (d) comprise bringing the adapter-target constructs in contact with a cleaving agent configured to cleave or excise the cleavable or excisable base.

According to some embodiments, the cleaving agent is selected from the group consisting of uracil DNA glycosylase (UDG), apyrimidinic/apurinic endonuclease (APE), endonucleases (e.g., endonuclease VIII (EndoVIII) or V (EndoV)), uracil-specific excision reagent (USER™) enzyme (a mixture of UDG and endonuclease VIII), formamidopyrimidine DNA glycosylase (Fpg), 8-oxoguanine glycosylase (OGG1), RNase (e.g., RNaseH, such as RNaseHII), ultraviolet light, and a combination thereof.

According to some embodiments, the oligonucleotide comprises a 3' region that is not complementary to the first strand of the adapters.

According to some embodiments, the polynucleotide adapters are a polynucleotide of the invention.

According to some embodiments, the target double-stranded polynucleotides are selected from the group consisting of genomic DNA or a fragment thereof, cell-free DNA, and cDNA.

According to some embodiments, the target double-stranded polynucleotides are a plurality of target DNA molecules having different sequences.

According to some embodiments, the method produces a library of different double-stranded polynucleotide molecules each comprising regions of non-complementarity at a 5' end and a 3' end.

According to some embodiments, the adapters are in excess of the different target double-stranded polynucleotides by a molar ratio of more than 200:1.

According to some embodiments, the subjecting in (d) further comprises subjecting an adapter dimer produced in (c) to the conditions sufficient to cleave or excise the cleavable or excisable bases, thereby degrading the adapter dimers.

According to some embodiments, the oligonucleotide comprises a capture moiety, and the method further comprises contacting the library with a capturing molecule under conditions sufficient for binding of the capturing molecule to the capture moiety and isolating the capturing molecule.

According to some embodiments, the oligonucleotide comprises a capture moiety 5' to at least one cleavable or excisable base, wherein the cleavable or excisable base in the oligonucleotide is cleaved or excised by different conditions than the cleavable or excisable bases in the second strand, and wherein excision of the cleavable bases from the oligonucleotide induces removal of the capture moiety from the polynucleotide of the library; and the method further comprises i. contacting the library with a capturing molecule under conditions sufficient for binding of the capturing molecule to the capture moiety;
ii. isolating the capturing molecule; and
iii. subjecting the isolated capturing molecule to conditions sufficient to cleave or excise the cleavable or excisable bases of the oligonucleotide, thereby dissociating the library polynucleotide from the capturing molecule.

According to some embodiments, the polynucleotide of the library is pre-bound to an enrichment solid support.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1A:
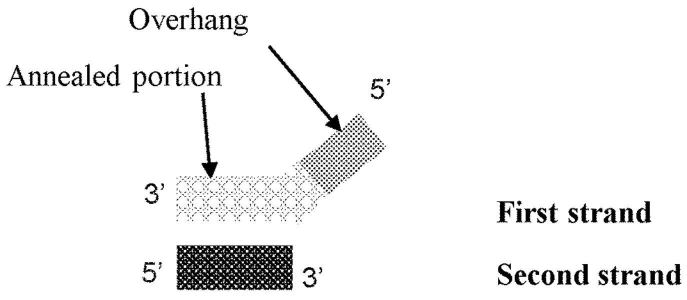
FIGS. 1A-1H are diagrams of various embodiments of the polynucleotides of the invention.

The present invention is directed to a method for preparing a library of polynucleotides.

As used herein, the term "library" refers to a plurality of polynucleotide molecules which share common sequences at their 5' ends and common sequences at their 3' ends. In some embodiments, the sequences and at the 5' end and the sequences at the 3' end are different sequences. In some embodiments, the different sequences are not complementary to each other. In some embodiments, the polynucleotide molecules are template for subsequent enzymatic reaction. In some embodiments, the enzymatic reaction is a polymerase reaction. In some embodiments, the enzymatic reaction is polymerization.

As used herein, the term "template" refers to that one or both strands of a polynucleotide are capable of acting as templates for template-dependent nucleic acid polymerization. In some embodiments, a template-dependent nucleic acid polymerization is catalyzed by a polymerase. In some embodiments, polymerization comprises elongation of a polymer by adjoining moieties, e.g., nucleotides, by formation of phosphor-diester bond(s).

The Polynucleotide

In some embodiments, the polynucleotide of the invention is a double-stranded polynucleotide comprising: a first strand comprising an annealed portion and an overhang portion; and a second strand comprising an annealed portion, wherein the second strand is complementary to and annealed to the annealed portion of the first strand.

As used herein, the term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated.

In some embodiments, the annealed portion of the second strand is a second annealed portion. In some embodiments, the second strand consists of the annealed portion. In some embodiments, the second strand consists essentially of the annealed portion. In some embodiments, the second strand comprises an annealed portion. In some embodiments, the second strand is perfectly complementary to the annealed portion of the first stand. In some embodiments, the annealed portion of the first strand and the second strand are perfectly complementary. Perfect complementarity or 100% complementarity refers to the situation in which each nucleotide unit of one polynucleotide strand can hydrogen bond with a nucleotide unit of a second polynucleotide strand. Less than perfect complementarity refers to the situation in which some, but not all, nucleotide units of two polynucleotide strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity. In some embodiments, the annealed portion of the first strand and the second strand comprises at least 70, 75, 80, 85, 90, 92, 93, 94, 95, 96, 97, 98, 99 or 100% complementarity. Each possibility represents a separate embodiment of the invention. In some embodiments, the second strand is devoid of a base not annealed to a base of the first strand. In some embodiments, the second strand comprises an overhang portion. In some embodiments, the overhang portion is a single base overhang. In some embodiments, the second strand overhang portion is on an opposite end of the polynucleotide from the first strand overhang portion.

In some embodiments, the second strand comprises an unmatched region compared to the first strand. In some embodiments, the unmatched region extends to the 5' end, the 3' end, or both, of the annealed portion. In some embodiments, the unmatched region of the second strand comprises at least one unmatched base. In some embodiments, the second strand comprises at least one base having an unmatched base to form hydrogen bonds, wherein the unmatched base is in the first strand. In some embodiments, the unmatched region of the second strand comprises 1 to 5 bases, 2 to 7 bases, 3 to 6 bases, 1 to 6 bases, 3 to 5 bases, or 1 to 8 bases. Each possibility represents a separate embodiment of the invention. In some embodiments, the unmatched region.

In general, there should be no upper limit to the length of the unmatched region. For clarity, an upper limit on the length of the unmatched region will typically be determined by function. In some embodiments, the unmatched region can be further extended in length as long as the unmatched region bears no functionality, including, but not limited to binding of a primer, primer extension, PCR, sequencing, or any combination thereof.

In some embodiments, the annealed portion of the first strand is a first annealed portion. In some embodiments, the overhang portion is an overhang region. As used herein, the term "overhang" refers to a single stranded region that is adjacent to a double stranded region on one side and not adjacent to any double stranded region on the other side. In some embodiments, the overhang portion is a first overhang portion. In some embodiments, the overhang portion is a 5' overhang. In some embodiments, the overhang portion is a 3' overhang. In some embodiments, the first strand comprises a second overhang. In some embodiments, the second overhang is on an opposite end of the first strand from the first overhang. In some embodiments, the second overhang is a single base overhang.

In some embodiments, the overhang portion comprises at least 6 nucleotides, at least 7 nucleotides, at least 8 nucleotides, at least 9 nucleotides, at least 10 nucleotides, at least 15 nucleotides, at least 20 nucleotides, or any value and range therebetween. Each possibility represents a separate embodiment of the invention. In some embodiments, the overhang portion comprises at least 9 nucleotides. In some embodiments, the overhang portion comprises at most 10, 15, 20, 25, 30, 35, 40, 45, 50, 55, 60, 65, 70, 75, 80, 85, 90, 95 or 100 nucleotides. Each possibility represents a separate embodiment of the invention. In some embodiments, the overhang does not comprise secondary structure. In some embodiments, the overhang does not comprise secondary structure that interferes with primer binding, polymerase progression or both. In some embodiments, the overhang portion comprises 9-15, 9-20, 9-25, 9-30, 9-35, 9-40, 9-45, 9-50, 10-15, 10-20, 10-25, 10-30, 10-35, 10-40, 10-45, 10-50, 12-15, 12-20, 12-25, 12-30, 12-35, 12-40, 12-45, 12-50, 13-15, 13-20, 13-25, 13-30, 13-35, 13-40, 13-54, 13-50, 14-15, 14-20, 14-25, 14-30, 14-35, 14-40, 14-45, 14-50, 15-20, 15-25, 15-30, 15-35, 15-40, 15-45 or 15-50 nucleotides. Each possibility represents a separate embodiment of the invention.

In some embodiments, a 3'-end overhang is at a 3' end of the first strand. In some embodiments, a 5'-end overhang is at a 5' end of the first strand. In some embodiments, the first strand comprises a 5'-end overhang and a 3'-end overhang. In some embodiments, the overhang portion is a 5'-end overhang and the 3'-end overhang is a single base overhang. In some embodiments, the overhang portion is a 3'-end overhang and the 5'-end overhang is a single base overhang (e.g., where the 3'-end overhang comprises more than 1 base). In some embodiments, the single base is an adenine. In some embodiments, the single base is a thymine.

In some embodiments, the overhang comprises a high melting temperature. In some embodiments, the overhang comprises a relatively higher melting temperature as compared to a strand of the annealed region. In some embodiments, higher comprises as least 1, 2, 3, 5, 7, 10, 15, 20, 25, 30, 35, 40, 45, 50, 55, 60, 65, 70, 75, 80, 85, 90, 95 or 100% higher melting temperature. Each possibility represents a separate embodiment of the invention. In some embodiments, higher comprises at least 1, 2, 3, 4, 5, 6, 7, 8, 9, 10, 12, 14, 15, 16, 18, 20, 22, 24, 25, 26, 28, 30, 32, 34, 36, 38, 40, 42, 44, 45, 46, 48 or 50 degrees Celsius higher. Each possibility represents a separate embodiment of the invention.

In some embodiments, the annealed region, or one strand of the annealed region (i.e., the first annealed region or the second annealed region), comprises a low melting temperature. In some embodiments, the annealed region, or one strand of the annealed region, comprises a relatively lower melting temperature as compared to the overhang region. In some embodiments, lower comprises as least 1, 2, 3, 5, 7, 10, 15, 20, 25, 30, 35, 40, 45, 50, 55, 60, 65, 70, 75, 80, 85, 90, 95 or 97% lower melting temperature. Each possibility represents a separate embodiment of the invention. In some embodiments, lower comprises at least 1, 2, 3, 4, 5, 6, 7, 8, 9, 10, 12, 14, 15, 16, 18, 20, 22, 24, 25, 26, 28, 30, 32, 34, 36, 38, 40, 42, 44, 45, 46, 48 or 50 degrees Celsius lower. Each possibility represents a separate embodiment of the invention.

Figure 1B:
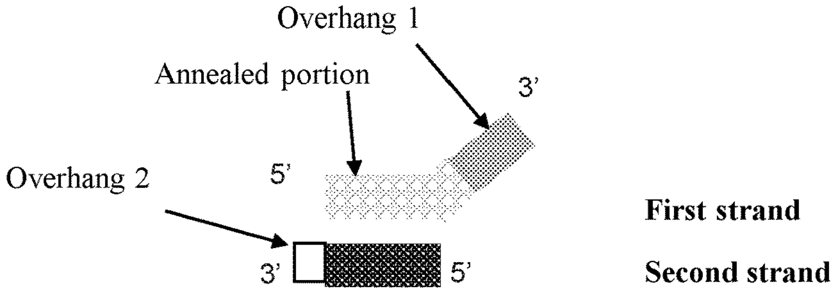
Figure 1C:
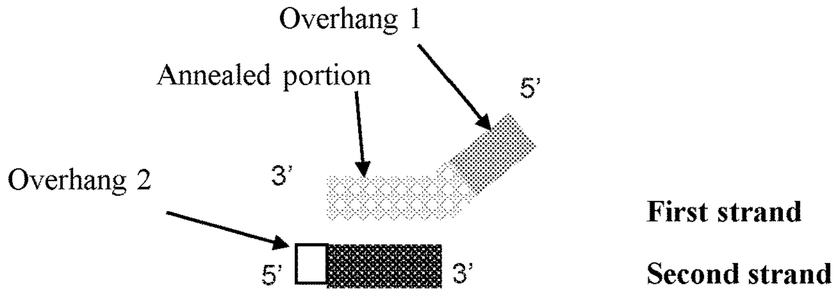
Figure 1D:
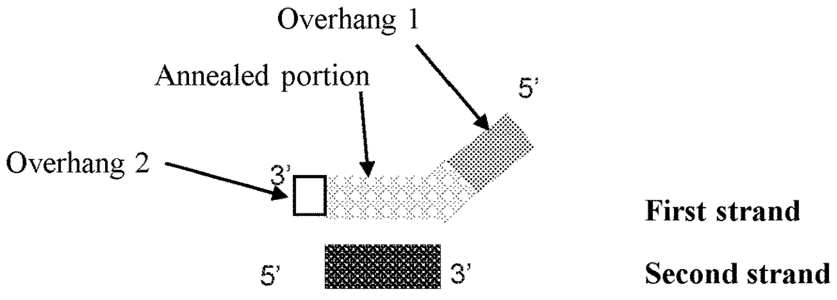

In some embodiments, the second strand comprises no overhang (FIG. 1A). In some embodiments, the second strand comprises an overhang at its 3' end and the overhang of the first strand is at its 3' end (FIG. 1B). In some embodiments, the second strand comprises an overhang at its 5' end and the overhang of the first strand is at its 5' end (FIG. 1C). In some embodiments, the overhang of the second strand is a single base overhang. In some embodiments, the single base is an adenine. In some embodiments, the single base is a thymine. In some embodiments, a single 'A' nucleotide may be added to a 3' end of the polynucleotide. In some embodiments, the single 'A' is at a 3' end of the first strand. In some embodiments, the single 'A' is at a 3' end of the second strand. In some embodiments, a single 'T' nucleotide may be added to a 3' end of the polynucleotide. In some embodiments, the single 'T' is at a 3' end of the first strand. In some embodiments, the single 'T' is at a 3' end of the second strand. In some embodiments, the second strand comprises an overhang on the side that is to anneal to a target dsDNA. In some embodiments, the first strand comprises a second overhang at the opposite end to the first overhang (FIG. 1D).

In some embodiments, each of the annealed portion of the first strand, the annealed portion of the second strand, or both, comprises at least 10 nucleotides, at least 15 nucleotides, at least 20 nucleotides, at least 25 nucleotides, at least 30 nucleotides, at least 35 nucleotides, at least 40 nucleotides, at least 45 nucleotides, at least 50 nucleotides, at least 55 nucleotides, at least 60 nucleotides, at least 65 nucleotides, or any value and range therebetween. Each possibility represents a separate embodiment of the invention. In some embodiments, each of the annealed portion of the first strand, the annealed portion of the second strand, or both, comprises at most 20 nucleotides, comprises at most 25 nucleotides, comprises at most 30 nucleotides, comprises at most 35 nucleotides, comprises at most 40 nucleotides, comprises at most 45 nucleotides, comprises at most 50 nucleotides, at most 55 nucleotides, comprises at most 60 nucleotides, at most 65 nucleotides, at most 70 nucleotides, at most 75 nucleotides, at most 80 nucleotides, at most 85 nucleotides, at most 90 nucleotides, at most 95 nucleotides, at most 100 nucleotides, or any value and range therebetween. Each possibility represents a separate embodiment of the invention. In some embodiments, each of the annealed portion of the first strand, the annealed portion of the second strand, or both, comprises 10-30, 10-40, 10-50, 10-55, 10-60, 10-65, 10-70, 15-30, 15-40, 15-50, 15-55, 15-60, 15-65, 15-70, 20-30, 20-40, 20-50, 20-55, 20-60, 20-65, 20-70, 25-30, 25-40, 25-50, 25-55, 25-60, 25-65, 25-70, 30-40, 30-50, 30-55, 30-60, 30-65, 30-70, 35-40, 35-50, 35-55, 35-60, 35-65, 35-70, 40-50, 40-55, 40-60, 40-65, or 40-70 nucleotides. Each possibility represents a separate embodiment of the invention.

In some embodiments, the annealed portion of the first strand and the annealed portion of the second strand consist of the same number of nucleotides. In some embodiments, the annealed portion of the first strand and the annealed portion of the second strand consist of a different number of nucleotides. In some embodiments, the first strand annealed portion comprises more nucleotides than the annealed portion of the second strand. In some embodiments, the second strand annealed portion comprises more nucleotides than the annealed portion of the first strand. In some embodiments, the 3' end and the 5' end of the anneals portion of both strands is annealed, and in the between there are non-annealed nucleotides on the first strand, the second strand or both.

In some embodiments, the two strands of the adapter are 100% complementary in the double-stranded region. It will be appreciated that one or more nucleotide mismatches may be tolerated within the double-stranded region, provided that the two strands are capable of forming a stable duplex under standard ligation conditions.

Adapters for use in the invention will generally include a double-stranded region adjacent to the "ligatable" end of the adapter, i.e. the end that is joined to a target polynucleotide in the ligation reaction. The ligatable end of the adapter may be blunt or, in other embodiments, short 5' or 3' overhangs of one or more nucleotides may be present to facilitate/promote ligation. In some embodiments, the ligatable ends comprise a single nucleotide overhang of thymidine/adenosine end, e.g., so as to facilitate T/A cloning. The 5' terminal nucleotide at the ligatable end of the adapter should be phosphorylated to enable phosphodiester linkage to a 3' hydroxyl group on the target polynucleotide. In some embodiments, the target polynucleotide duplex or molecule is devoid of phosphorylated 5'-ends. In some embodiments, the target polynucleotide duplex or molecule is dephosphorylated. In some embodiments, the method of the invention comprises a step of dephosphorylating the target polynucleotide duplex or molecule. Methods for dephosphorylating polynucleotide molecules would be apparent to one of ordinary skill in the art of molecular biology. Non-limiting example for dephosphorylating a polynucleotide would include incubating the target polynucleotide molecule with a phosphatase, e.g., calf intestinal phosphatase (CIP) under optimal conditions for the CIP enzyme. In some embodiments, a first nucleotide at a 5' end of the first strand lacks a free phosphate group. In some embodiments, a first nucleotide at a 3' end of the first strand lacks a free phosphate group. In some embodiments, a first nucleotide at a 5' end of the second strand lacks a free phosphate group. In some embodiments, a first nucleotide at a 3' end of the second strand lacks a free phosphate group. In some embodiments, a first nucleotide at a 5' end of the first strand comprises a free hydroxy (OH) group. In some embodiments, the OH group is a 5' hydroxy group. In some embodiments, a first nucleotide at a 5' end of the second strand comprises a free OH group. In some embodiments, a first nucleotide at a 3' end of the first strand comprises a free OH group. In some embodiments, a first nucleotide at a 3' end of the second strand comprises a free OH group.

In some embodiments, at least one strand is 3' blocked. As used herein, the term "3' blocked" refers to a nucleotide that cannot be extended at its 3' end by a polymerase. In some embodiments, a 3' blocked strand comprises a 3' modification or modified base. In some embodiments, the modification is a blocking modification. In some embodiments, the modified base is a blocked base. In some embodiments, a blocked base is a base to which polymerase cannot link a new base. In some embodiments, linking is polymerizing on a new base. In some embodiments, a blocked base is selected from a monophosphate nucleotide, a dideoxynucleotide and a 3' hexanediol modified base. In some embodiments, a blocked base is a monophosphate nucleotide. In some embodiments, a blocked base is dideoxynucleotide. In some embodiments, a blocked base is a 3' hexanediol modified base. In some embodiments, the overhang portion is a 5'-end overhang. In some embodiments, the first nucleotide at the 5'-end of the second strand is a monophosphate nucleotide. In some embodiments, the first nucleotide at the 3'-end of the second strand is a monophosphate nucleotide. In some embodiments, the overhang portion is a 5'-end overhang, and the first nucleotide at the 5'-end of the second strand is a monophosphate nucleotide. In some embodiments, the overhang portion is a 5'-end overhang, and the first nucleotide at the 3'-end of the second strand is a monophosphate nucleotide. In some embodiments, the overhang portion is a 3'-end overhang. In some embodiments, the first nucleotide from the 3'-end of the second strand is a dideoxynucleotide. In some embodiments, the first nucleotide from the 5'-end of the second strand is a dideoxynucleotide. In some embodiments, the overhang portion is a 3'-end overhang, and the first nucleotide from the 5'-end of the second strand is a dideoxynucleotide. In some embodiments, the overhang portion is a 3'-end overhang, and the first nucleotide from the 3'-end of the second strand is a dideoxynucleotide. In some embodiments, the overhang portion is a 5'-end overhang, and the first nucleotide from the 3'-end of the second strand is a dideoxynucleotide. In some embodiments, the overhang portion is a 5'-end overhang, and the first nucleotide from the 5'-end of the second strand is a dideoxynucleotide. In some embodiments, the first nucleotide from the 3'-end of the second strand is a 3' hexanediol modified base. In some embodiments, the first nucleotide from the 5'-end of the second strand is a 3' hexanediol modified base. In some embodiments, the overhang portion is a 3'-end overhang, and the first nucleotide from the 5'-end of the second strand is a 3' hexanediol modified base. In some embodiments, the overhang portion is a 3'-end overhang, and the first nucleotide from the 3'-end of the second strand is a 3' hexanediol modified base. In some embodiments, the overhang portion is a 5'-end overhang, and the first nucleotide from the 3'-end of the second strand is a 3' hexanediol modified base. In some embodiments, the overhang portion is a 5'-end overhang, and the first nucleotide from the 5'-end of the second strand is a 3' hexanediol modified base.

In some embodiments, the second strand is un-extendable. The terms "un-extendable", "non-extendable" or "blocked" are interchangeable and refer to that a polynucleotide cannot be further polymerized by formation of phosphodiester bonds. In some embodiments, polymerization is template dependent or independent. In some embodiments, polymerization is enzyme dependent or independent. An un-extendable polynucleotide which can be used according to the method of the invention can be produced or comprise chemically modified nucleotides according to any method known in the art of molecular biology. In some embodiments, a 3' hexanediol modified base renders a polynucleotide "un-extendable". In some embodiments, dideoxynucleotide renders a polynucleotide "un-extendable". In some embodiments, an un-extendable polynucleotide comprises a dideoxynucleotide. In some embodiments, an un-extendable polynucleotide comprises a 3' hexanediol modified base. In some embodiments, the chemically modified nucleotides, e.g., a dideoxynucleotide or 3' hexanediol modified base, is located at the 3'-end of the un-extendable polynucleotide. In some embodiments, the first strand comprises a 5' overhang and the second strand is 3' blocked.

In some embodiments, a second strand of the polynucleotide of the invention is un-extendable and results in only a single stranded DNA molecule of a chimeric DNA molecule (SSCDM) annealed to a single stranded DNA oligonucleotide being extended. This tightly controlled extension reduces the probability of continuous extension and production of a single template comprising multiple target polynucleotides.

The precise nucleotide sequences of the annealed regions are generally not material to the invention and may be selected by the user. In some embodiments, one strand of the annealed region at least comprises "primer-binding" sequences which enable specific annealing of amplification primers when the templates are in use in a solid-phase amplification reaction. In some embodiments, the annealed region of the first strand comprises the primer binding sequence. In some embodiments, the annealed region of the second strand comprises the primer binding sequence. The primer-binding sequences are thus determined by the sequence of the primers to be ultimately used for solid-phase amplification. The sequence of these primers in turn is advantageously selected to avoid or minimize binding of the primers to the target portions of the templates within the library under the conditions of the amplification reaction, but is otherwise not particularly limited. By way of example, if the target portions of the templates are derived from human genomic DNA, then the sequences of the primers to be used in solid phase amplification should ideally be selected to minimize non-specific binding to any human genomic sequence. In some embodiments, the primers do not bind to a sequence found in nature. In some embodiments, the primers do not bind to a sequence found in a target cell. In some embodiments, the cell is a mammalian cell. In some embodiments, the mammal is a human.

The precise nucleotide sequence of the adapters is generally not material to the invention and may be selected by the user such that the desired sequence elements are ultimately included in the common sequences of the library of templates derived from the adapters, for example to provide binding sites for particular sets of universal amplification primers and/or sequencing primers. Additional sequence elements may be included, for example to provide binding sites for sequencing primers which will ultimately be used in sequencing of template molecules in the library, or products derived from amplification of the template library, for example on a solid support. The adapters may further include "tag" sequences, which can be used to tag, or mark template molecules derived from a particular source. In some embodiments, the tag is a barcode.

In some embodiments, the annealed region of the first strand, second strand, or both, comprises a barcode. In some embodiments, the barcode is a nucleotide barcode. In some embodiments, the annealed region of the first strand, second strand, or both, comprises a barcode nucleotide sequence. In some embodiments, the annealed region of the first strand, second strand, or both, comprises a portion of a barcode nucleotide sequence. In some embodiments, the annealed region of the first strand, second strand, or both, comprises a sequence complementary to a barcode nucleotide sequence. In some embodiments, the annealed region of the first strand, second strand, or both, comprises a portion of a sequence complementary to a barcode nucleotide sequence. In some embodiments, the first strand comprises a barcode nucleotide sequence, and the barcode nucleotide sequence extends from the annealed portion into the overhang portion. In some embodiments, the second strand comprises a barcode nucleotide sequence. In some embodiments, the second strand comprises a reverse complement of a barcode nucleotide sequence. Barcode sequences are well known in the art and any such barcode may be used. In some embodiments, the barcode is a sequence not expressed in a target cell. In some embodiments, the barcode is a sequence not expressed in the template nucleic acid molecules. In some embodiments, the barcode is a sequence not expressed in nature.

In some embodiments, a portion is at least 25, 30, 40, 50, 60, 70, 75, 80, 90, 95, 97, 99 or 100%. Each possibility represents a separate embodiment of the invention. In some embodiments, a portion is at least 50%. In some embodiments, a portion is at least 70%. In some embodiments, a portion is at least 90%. In some embodiments, a portion is less than 100%.

In one embodiment, the barcode is one or more nucleic acid molecules. In some embodiments, the barcode is a unique molecular identifier (UMI). In some embodiments, the first strand comprises an UMI. In some embodiments, the second strand comprises an UMI. In some embodiments, the second strand comprises a reverse complement of an UMI. In some embodiments, the annealed region comprises an UMI. In some embodiments, the overhang region comprises an UMI. In some embodiments, the overhang region comprises a barcode. In some embodiments, the UMI extends from the annealed region to the overhang region. In some embodiments, the barcode extends from the annealed region to the overhang region. Nucleic acid molecules, such as DNA strands, present an unlimited number of barcoding options. As used throughout the invention "barcode", and "DNA barcode", are interchangeable with each other and have the same meaning. The nucleic acid molecule serving as a DNA barcode is a polymer of deoxynucleic acids or ribonucleic acids or both and may be single-stranded or double-stranded, optionally containing synthetic, non-natural or altered nucleotide bases. In some embodiments, the nucleic acid molecule is labeled, for instance, with biotin, a radiolabel, or a fluorescent label. Barcodes are well known in the art, and any such barcodes may be used for the performance of the invention.

As will be appreciated by a person skilled in the art, incorporation of unique DNA barcodes into the polynucleotide of the invention (e.g., the adapter) which is ligated to a pool or pools of nucleic acid, such as comprising nucleic acid molecules from different sources, allows the identification of individual or particular nucleic acid source without having to individually sorting each nucleic acid source from the pool, while using assays including, but not limited to, microarray systems, PCR, nucleic acid hybridization (including "blotting") or high throughput sequencing.

In some embodiments, the barcode comprises or consists of a sequence not found in nature. In another embodiment, the barcode comprises or consists of a sequence which is not substantially identical or complementary to a cell's genomic material (such as to prevent non-specific amplification of an endogenous nucleic acid molecule within a cell's genomic material, e.g., preventing false positive amplification results). In some embodiments, the cell is a mammalian cell. In some embodiments, the mammal is a human. In some embodiments, the barcode is not a full genome. In some embodiments, the barcode is not a chromosome. In some embodiments, the barcode does not have equal to or more than 60%, 65%, 70%, 75%, 80%, 85%, 90%, 95%, 97%, 99% or 100% complementarity to a naturally occurring sequence, or any value and range therebetween. Each possibility represents a separate embodiment of the invention. In some embodiments, the barcode comprises less than 60%, 55%, 50%, 45%, 40%, 35%, 30%, 25%, 20%, 15%, 10%, 5%, 3%, or 1% complementarity to a naturally occurring sequence, or any value and range therebetween. Each possibility represents a separate embodiment of the invention.

In some embodiments, a unique barcode is suitable for identifying a specific or particular subpopulation of nucleic acid molecules within a heterogenous pool of different nucleic acid molecules implementing the methods disclosed by the present the invention. Methods for the detection of the presence and identification of a nucleic acid molecule or sequence are known to a skilled artisan and include sequencing and array (e.g., microarray) systems capable of enhancing the presence of multiple barcodes.

In some embodiments, the overhang region comprises a sequence complementary to a 3' region of a nucleic acid primer. In some embodiments, the first stand annealed region comprises a sequence complementary to a 3' region of a nucleic acid primer. In some embodiments, the second stand annealed region comprises a sequence complementary to a 3' region of a nucleic acid primer.

As used herein, the term "primer" includes an oligonucleotide, either natural or synthetic, that is capable, upon forming a duplex with a polynucleotide template, of acting as a point of initiation of nucleic acid synthesis and being extended from its 3' end along the template so that an extended duplex is formed. Primers within the scope of the present invention bind adjacent to a target sequence. A "primer" may be considered a short polynucleotide, generally with a free 3'-OH group that binds to a target or template potentially present in a sample of interest by hybridizing with the target, and thereafter promoting polymerization of a polynucleotide complementary to the target. Primers of the invention are comprised of nucleotides ranging from 8 to 35 nucleotides. In one embodiment, the primer is at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, at least 26 nucleotides, at least 27 nucleotides, at least 28 nucleotides, at least 29 nucleotides, at least 30 nucleotides, at least 31 nucleotides, at least 32 nucleotides, at least 33 nucleotides, at least 34 nucleotides, or at least 35 nucleotides long, or any value and range therebetween. Each possibility represents a separate embodiment of the invention. In one embodiment, the primer is 10 to 50 nucleotides, 5 to 40 nucleotides, 8 to 45 nucleotides, 20 to 35 nucleotides, 18 to 30 nucleotides, or 20 to 45 nucleotides long. Each possibility represents a separate embodiment of the invention.

In some embodiments, the primer hybridizes to the polynucleotide of the invention. In some embodiments, the primer hybridizes to a denatured polynucleotide of the invention. In some embodiments, the primer hybridizes to a nucleic acid molecule comprising the polynucleotide. In some embodiments, the primer hybridizes to a nucleic acid molecule ligated to the polynucleotide. In some embodiments, the primer hybridizes to an overhang of the first strand. In some embodiments, the primer hybridizes to the annealed portion of the first strand. In some embodiments, the primer hybridizes to the second strand. In some embodiments, the primer hybridizes to part of the annealed portion and part of the overhang of the first strand.

The term "hybridization" or "hybridizes" as used herein refers to the formation of a duplex between nucleotide sequences which are sufficiently complementary to form duplexes via Watson-Crick base pairing. Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T (U), G and C of one sequence is then aligned with a T (U), A, C and G, respectively, of the other sequence. RNA sequences can also include complementary G=U or U=G base pairs. Thus, two sequences need not have perfect homology to be "complementary" under the invention.

In some embodiments, the polynucleotide is DNA, RNA or a mixture of DNA and RNA. In some embodiments, the polynucleotide is cDNA. In some embodiments, the polynucleotide is LNA.

The terms "polynucleotide", "polynucleotide sequence", "nucleic acid sequence", and "nucleic acid molecule" are used interchangeably herein. These terms encompass nucleotide sequences and the like. A polynucleotide may be a polymer of RNA or DNA that is single- or double-stranded, that optionally contains synthetic, non-natural or altered nucleotide bases.

In some embodiments, the second strand comprises at least one cleavable or excisable base. In some embodiments, the first strand comprises at least one cleavable or excisable base. In some embodiments, the first or second strand comprises at least one cleavable or excisable base. In some embodiments, the overhang portion comprises at least one cleavable or excisable base. As used herein, the term "cleavable or excisable base" generally refers to any base or analog of a base (e.g., nucleobase) that can be specifically cleaved and removed or excised from a nucleic acid molecule. The terms "cleavable" and "excisable" as used herein are synonymous and interchangeable. The terms "cleavage" and "excision" as used herein are synonymous and interchangeable. Examples of cleavable bases include, but are not limited to, uracil, 8-oxoguanine (also referred to as 8-hydroxyguanine, 8-oxo-7,8-dihydroguanine, 7,8-dihydro-8-oxoguanine, and 8oxoG herein), inosine, and 2,6-diamino-4-hydroxy-5-formamidopyrimidine (FapyG). In some embodiments, the uracil is a DNA uracil. In some embodiments, the uracil is an RNA uracil. Cleavage and/or excision of a cleavable or excisable moiety may be carried out by contacting the cleavable or excisable moiety (e.g., cleavable base) with a cleaving agent. Examples of cleaving agents include, but are not limited to, uracil DNA glycosylase (UDG), apyrimidinic/apurinic endonuclease (APE), endonucleases (e.g., endonuclease VIII (EndoVIII) or V (EndoV)), uracil-specific excision reagent (USER™) enzyme (a mixture of UDG and endonuclease VIII), formamidopyrimidine DNA glycosylase (Fpg), 8-oxoguanine glycosylase (OGG1), and RNase (e.g., RNaseH, such as RNaseHII). Photocleavable or photoexcisable moieties may be cleaved or excised using appropriate application of energy, such as by contacting the moiety with UV light. In some embodiments, a cleavable or excisable moiety is a cleavable or excisable base. One or more cleaving agents may be used in combination to cleave or excise a cleavable or excisable moiety. In an example, the cleavable base may be an RNA base in a DNA backbone, and the cleaving agent may be RNase (e.g., RNaseH or RNaseHII). In such a case, the nucleic acid molecule may not be an RNA molecule. In some embodiments, the cleavable or excisable base is an RNA base and the nucleic acid molecule s devoid of RNA bases other than the cleavable or excisable base. In another example, the cleavable base may be a uracil DNA base and the cleaving agent may be selected from uracil DNA glycosylase (UDG), apyrimidinic/apurinic endonuclease (APE), Endonuclease VIII and uracil-specific excision reagent (USER™) enzyme (a mixture of UDG and endonuclease VIII). For example, the cleaving agent may be UDG. For example, the cleaving agent may be APE. In another example, the cleavable base may be an inosine base and the cleaving agent may be Endonuclease V (Endo V). In another example, the cleavable base may be 2,6-diamino-4-hydroxy-5-formamidopyrimidine (FapyG) base and the cleaving agent may be formamidopyrimidine DNA glycosylase (Fpg). In another example, the cleavable base may be 8-oxo-7,8-dihydroguanine (8oxoG) and the cleaving agent may be 8-oxoguanine glycosylase (OGG1). In another example, the cleavable base may be a photo-cleavable base and the cleaving agent may be light, such as laser light. Application of a cleaving agent may generate a "nick" in a strand of a nucleic acid molecule. Alternatively, or in addition to, another enzyme may be added to generate a nick, or otherwise functionalize a nick. For example, T4 pnk may be added to remove a 3' phosphate. An enzyme may be used to remove a lesion, such as a 3' lesion. In some embodiments, the cleavable or excisable base is an RNA base and the cleaving agent is RNase H. In some embodiments, the RNase H is RNase HII. In some embodiments, the RNA base is a uracil RNA base. In some embodiments, the cleavable or excisable base is a uracil DNA base and the cleaving agent is selected from a) UDG, b) UDG and an Endonuclease and c) USER™ (a mixture of UDG and endonuclease VIII). In some embodiments, the Endonuclease is Endonuclease VIII.

In some embodiments, the nucleic acid molecule is devoid of cleavable bases other than those recited herein. In some embodiments, a mixture of cleavable bases is used. In some embodiments, all cleavable bases used are the same type of cleavable base, and/or cleaved by the same cleaving agent. In embodiments wherein the cleavable base is an RNA base, the nucleic acid itself will not be of RNA. In some embodiments, a type of cleavable bases are cleavable bases that are cleaved under the same condition. In some embodiments, the same conditions are the same cleaving agent.

The first or second strand may include one or more cleavable or excisable moieties (e.g., one or more cleavable bases). Where a nucleic acid molecule includes more than one cleavable or excisable moieties, the cleavable or excisable moieties may be the same as or different than one another. For example, the second strand may comprise a first cleavable or excisable base and a second cleavable or excisable base, where the first cleavable or excisable base is different than the second cleavable or excisable base. The first cleavable or excisable base and the second cleavable or excisable base may be configured to be cleaved by the same cleaving agent or a combination of cleaving agents. In another example, the second strand may comprise a first cleavable or excisable base and a second cleavable or excisable base, where the first cleavable or excisable base and the second cleavable or excisable base are of a same type. In some embodiments, different cleavable or excisable bases are cleavable or excisable in different conditions. Thus, the conditions that will cleave/excise a first cleavable or excisable base will not cleave/excise a different cleavable or excisable base.

In some embodiments, the first and second strand do not both comprise a cleavable or excisable base. In some embodiments, the first and second strand both comprise a cleavable or excisable base. In some embodiments, the first strand comprises a first cleavable or excisable base and the second strand comprises a second cleavable or excisable base. In some embodiments, the first and second cleavable or excisable bases are different bases. In some embodiments, the first and second cleavable or excisable bases are cleaved or excised under different conditions. In some embodiments, the first strand and the second strand do not both comprises cleavable or excisable bases cleavable or excisable under the same conditions. In some embodiments, the first strand is devoid of cleavable or excisable bases that cleave or excise under conditions that cleave or excise cleavable or excisable bases in the second strand. In some embodiments, the second strand is devoid of cleavable or excisable bases that cleave or excise under conditions that cleave or excise cleavable or excisable bases in the first strand. In some embodiments, the second strand is devoid of the same kind of cleavable bases as are present in the first strand.

In some embodiments, in the first strand is in the overhang portion. In some embodiments, the first stand overhang comprises at least one cleavable or excisable base. In some embodiments, the first strand 5' overhang comprises at least one cleavable or excisable base. In some embodiments, the most 5' base (e.g., the base at the 5' end) of the first strand overhang is a cleavable or excisable base. In some embodiments, the most 3' base (e.g., the base at the 3' end) of the first strand overhang is a cleavable or excisable base. In some embodiments, the overhang of the first strand comprises a sufficient number of cleavable or excisable bases, sufficiently close to each other, such that excision of the cleavable or excisable bases induces dissociation of the first strand overhang from a reverse complement of the first strand overhang. It will be understood by a skilled artisan that, as the overhang is single-stranded, excision of any base in the overhang will result in dissociation of all of the overhang that is no longer attached to the complementary region. However, once the polynucleotide of the invention has been incorporated into a chimeric polynucleotide, a second strand region complementary to the overhang may be synthesized. In such a case the cleavable or excisable bases will be in sufficient number and distance such that excision of the cleavable ore excisable base induces dissociation of the overhang region from its reverse complement.

In some embodiments, the at least one cleavable or excisable base is proximal to a 5' end, proximal to a 3' end or both. In some embodiments, the at least one cleavable or excisable base is proximal to a 5' end. In some embodiments, the at least one cleavable or excisable base is proximal to a 3' end. In some embodiments, the at least one cleavable or excisable base is proximal to a 5' end and a 3' end. In some embodiments, proximal is within 0, 1, 2, 3, 4, 5, 6, 7, 8, 9 or 10 bases. Each possibility represents a separate embodiment of the invention. In some embodiments, proximal is within 7 bases. In some embodiments, proximal is within 5 bases. In some embodiments, proximal is within 3 bases. In some embodiments, proximal is 0, 1, 2 or 3 bases. In some embodiments, proximal is proximal to an end. Thus 0 bases proximal to the end refers to the base at the end as it is zero from the end. 1 base proximal to the end refers to the base adjacent to the base at the end, and so on.

In some embodiments, proximal to an end is sufficiently close to the end such that excision of the cleavable base induces all bases between the cleavable base and the end to dissociate from the other strand (i.e. the first strand). In some embodiments, the other strand is the first strand. It will be understood by a skilled artisan that when a nick, gap or hole is made in one side of a double stranded molecule that this generates instability in the cut strand. If there is sufficient base-pairing with the uncut strand, all the bases will stay attached. However, when only a few bases in a row are attached this can lead to sufficient instability that causes these few bases to dissociate. Stability can be modulated by conditions other than just the number of base-paired nucleotides in a row. These conditions include temperature, pH, and salt levels. By altering these conditions, a skilled artisan can cause disassociate of a longer stretch of nucleotides (e.g., more than 5, more than 6, more than 7, more than 8, more than 9, more than 10, more than 12, more than 15, more than 20 nucleotides) or can cause a shorter stretch to stay associated (e.g., even as few at 5, 4, 3, 2, or even 1 nucleotide).

Where a cleavable or excisable base is proximal to an end of the strand, cleavage or excision of the base may induce one or more other bases to dissociate from the nucleic acid molecule. For example, a cleavable or excisable base may be disposed proximal to a free end of a strand of a nucleic acid molecule (e.g., within 0, 1, 2, 3, 4, or 5 bases of the end of the first strand), and cleavage or excision of the cleavable or excisable base may induce one or more bases of the strand of the nucleic acid molecule to dissociate from the strand (e.g., one or more bases at or proximal to the end of the second strand). Dissociation may result from instability generated in the cleaved or excised strand in the form of, e.g., a nick, gap, or hole. If there is sufficient base-pairing with the uncut strand all the bases are likely to stay attached. However, when only a few bases in a row are coupled to bases in another strand, such as near an end of a strand of a double-stranded nucleic acid molecule, this instability may be sufficient to cause these few bases to dissociate. This may also occur when two nicks are created (e.g., by excision of two bases) and the number of bases in between dissociates due to instability.

Figure 1E:
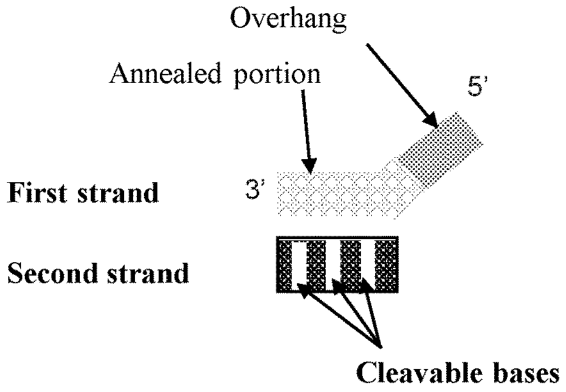

The double-stranded nucleic acid molecule may comprise at least two cleavable or excisable bases on the second strand (FIG. 1E). The at least two cleavable or excisable moieties bases may be a plurality of cleavable or excisable bases. In some embodiments, the second strand comprises a plurality of cleavable or excisable bases. In some embodiments, a plurality of cleavable or excisable bases is at least 2, 3, 4, 5, 6, 7, 8, 9, or 10 bases. Each possibility represents a separate embodiment of the invention.

In some embodiments, the at least two cleavable bases are sufficiently close to each other that excision dissociates an intervening base. In some embodiments, the at least two cleavable bases are sufficiently close to each other that excision dissociates intervening bases. In some embodiments, the at least two cleavable bases are sufficiently close to each other that excision dissociates all intervening bases. In some embodiments, the two cleavable bases are proximal to each other. In some embodiments, cleavage of the cleavable bases induces dissociation of the second strand from the first strand. In some embodiments, dissociates is from a complementary strand. In some embodiments, cleavage of the cleavable bases induces complete dissociation of the second strand from the first strand. In some embodiments, cleavage of the cleavable bases produces a single stranded polynucleotide consisting of the first strand. In some embodiments, cleavage of the cleavable bases converts the double stranded polynucleotide to a single-stranded molecule consisting of the first strand. In some embodiments, cleavage of the cleavable bases converts the double stranded polynucleotide to a single-stranded molecule consisting of the first strand and a single stranded second strand. In some embodiments, the single-stranded second strand is a degraded second strand. In some embodiments, the second strand comprises a sufficient number of cleavable bases such that excision of the cleavable bases induces dissociation of the second strand from the first strand. In some embodiments, the second strand comprises at least two cleavable bases sufficiently close to each other that excision of said cleavable bases induces dissociation of the second strand from the first strand. In some embodiments, the second strand comprises a sufficient number of cleavable bases, sufficiently close to each other, such that excision of the cleavable bases induces dissociation of the second strand from the first strand.

In some embodiments, sufficiently close is a sufficient distance such that excision does dissociate an intervening base. In some embodiments, sufficiently close is a sufficient distance such that excision does dissociate intervening bases. In some embodiments, sufficiently close is a sufficient distance such that excision does all intervening bases. In some embodiments, an intervening base is a plurality of intervening bases. In some embodiments, an intervening base is all intervening bases. In some embodiments, a sufficient distance such that excision does dissociate an intervening base is less than 30, 25, 20, 18, 16, 15, 14, 12, 10, 9, 8, 7, 6, 5, 4, 3, 2 or 1 bases. Each possibility represents a separate embodiment of the invention. In some embodiments, a sufficient distance such that excision does dissociate an intervening base is less than 10 bases. In some embodiments, a sufficient distance such that excision does dissociate an intervening base is not more than 3 bases. In some embodiments, a sufficient distance such that excision does dissociate an intervening base is not more than 5 bases. In some embodiments, a sufficient distance such that excision does dissociate an intervening base is not more than 7 bases. In some embodiments, a sufficient distance such that excision does dissociate an intervening base is not more than 6 bases.

It will be understood by a skilled artisan that the number of cleavable bases and the distance between them will depend on the conditions and how strong the binding of the two strands must be to stop dissociation. In some embodiments, the second strand comprises 16 or fewer bases. In some embodiments, the second strand comprises 16 or fewer bases and 3 or more cleavable bases. In some embodiments, the second strand comprises 16 or fewer bases and 2 or more cleavable bases. In some embodiments, the second strand comprises 21 or fewer bases and 4 or more cleavable bases. In some embodiments, the second strand comprises 21 or fewer bases and 3 or more cleavable bases. In some embodiments, the second strand is devoid of a stretch of non-cleavable or excisable bases of sufficient length that excision of the cleavable or excisable bases does not induce dissociation of the stretch from the first strand. It will be understood that the second strand need only be long enough to include the reverse complement of the barcode, UMI or both and should not be significantly longer. Extra bases are wasteful as they will be dissociated and lost. The second strand needs to be long enough to give stability to the whole molecule and keep it associated with the first strand during adapter binding and at least until cleavage and dissociation.

Figure 1F:
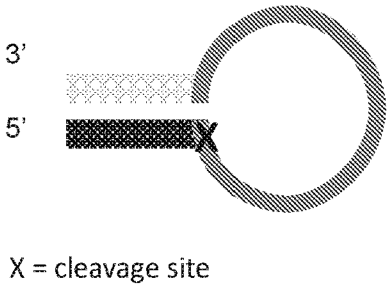
Figure 1G:
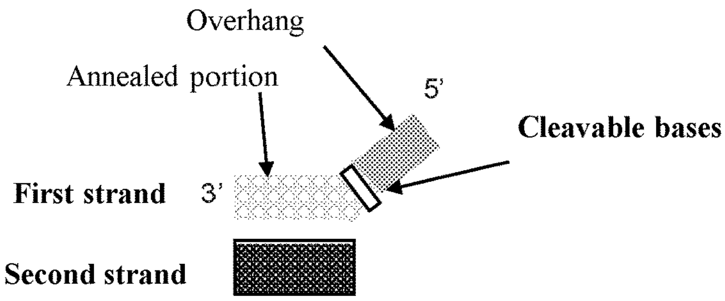
Figure 1H:
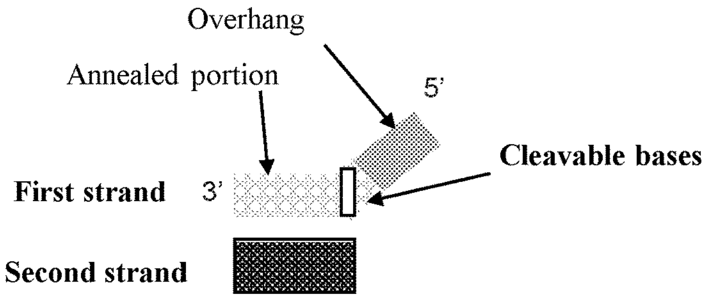

In some embodiments, the first strand comprises at least one cleavable or excisable base. In some embodiments, the first strand comprises a cleavable or excisable base in the overhang (FIG. 1G). In some embodiments, the first strand comprises a plurality of cleavable or excisable bases in the overhang. In some embodiments, the first strand comprises at least one cleavable or excisable base in the annealed region. In some embodiments, the at least one cleavable or excisable base in the annealed region is proximal to the overhang region. In some embodiments, cleavage or excision of the cleavable or excisable base results is dissociation of a portion of the overhang from the polynucleotide of the invention. In some embodiments, a portion is all of the overhang. In some embodiments, the cleavable or excisable base is the first base of the overhang (FIG. 1G). In some embodiments, the first base of the overhang is the base adjacent to the annealed region. In some embodiments, the cleavable or excisable base is the last base of the annealed region (FIG. 1H). In some embodiments, the last base is the base adjacent to the overhang. It will be understood by a skilled artisan that since the overhang is hybridized to no second strand, cleavage of a base in the overhang will result in removal of all the bases beyond that cleavage point. Further, if cleavage occurs in the double stranded region but is close enough to the overhang such that the intervening bases are destabilized, the overhang as a whole will dissociate. Further, if the last base of the double stranded region or the first base of the overhang is cleaved, the entire overhang will be removed. In some embodiments, the first strand is devoid of a stretch of non-cleavable or excisable bases of sufficient length that excision of the cleavable or excisable bases does not induce dissociation of the stretch from a complementary strand. In some embodiments, the overhang portion is devoid of a stretch of non-cleavable or excisable bases of sufficient length that excision of the cleavable or excisable bases does not induce dissociation of the stretch from a complementary strand.

By another aspect, there is provided a composition comprising: the polynucleotide of the invention, and any one of a solitary purine, a solitary pyrimidine, a DNA ligase, an RNA ligase, a DNA polymerase, an RNA polymerase, a cleaving agent and any combination thereof.

In some embodiments, the composition comprises a solitary purine. In some embodiments, the composition comprises a solitary pyrimidine. In some embodiments, the composition comprises a solitary purine and a solitary pyrimidine. In some embodiments, the composition comprises a ligase. In some embodiments, the ligase is a DNA ligase. In some embodiments, the ligase is an RNA ligase. In some embodiments, the composition comprises a polymerase. In some embodiments, the polymerase is a DNA polymerase. In some embodiments, the polymerase is an RNA polymerase. In some embodiments, the composition comprises a cleaving agent.

The polynucleotide molecules are preferably formed from two strands of DNA but may include mixtures of natural and non-natural nucleotides (e.g., one or more ribonucleotides) linked by a mixture of phosphodiester and non-phosphodiester backbone linkages. Other non-nucleotide modifications may be included such as, for example, biotin moieties, blocking groups and capture moieties for attachment to a solid surface, as discussed in further detail below.

In some embodiments, the double-strand oligonucleotide is generated by annealing the first and second strands. In some embodiments, a single strand of nucleic acid comprises both strands with a cleavage site, or nick (FIG. 1F). The cleavage site or nick is at a position that will be the end of the second strand closes to the overhang of the first strand. Cleavage at the site or nick produces the duplex polynucleotide (adapter) of the invention. In some embodiments, the region that will be the overhang does not comprise secondary structure and thus is a loop extending from the annealed region. In some embodiments, this single strand precursor molecule is a hairpin. Cleavage of the hair pin produces the overhang, double-stranded adapter of the invention.

In some embodiments, the polynucleotide of the invention comprises a capture moiety. In some instances, the capture moiety may comprise biotin (B), such that the primer molecule is biotinylated. In some instances, the capture moiety may comprise a capture sequence (e.g., nucleic acid sequence). In some instances, a sequence of the primer molecule may function as a capture sequence. In other instances, the capture moiety may comprise another nucleic acid molecule comprising a capture sequence. In some instances, the capture moiety may comprise a magnetic particle capable of capture by application of a magnetic field. In some instances, the capture moiety may comprise a charged particle capable of capture by application of an electric field. In some instances, the capture moiety may comprise one or more other mechanisms configured for, or capable of, capture by a capturing molecule. As used herein, a capture moiety is a molecule that can be isolated by binding to a capturing molecule. For example, the oligonucleotide can be conjugated to biotin (capture moiety) and then captured by a streptavidin column (the capturing molecule). Any capturing system may be used so that the polynucleotide can be isolated.

Methods

According to another aspect, there is provided a method for generating a library comprising: providing a plurality of target polynucleotide duplexes; providing a polynucleotide adapter, wherein the adapter comprises: (i) a double-stranded annealed region comprising complementarity between a first and second strand and wherein the second strand comprises the region of complementarity; (ii) and an overhang region on the first strand of the adapter; ligating the double-stranded annealed regions of the polynucleotide adapter to both ends of the target polynucleotide duplexes to form adapter-target constructs; denaturing the adapter-target constructs; annealing an oligonucleotide to the second strand region of complementarity of the denatured adapter-target constructs; and extending the annealed oligonucleotide to produce extension products complementary to the adapter-target constructs; thereby generating a library of polynucleotide molecules.

According to another aspect, there is provided a method for generating a library, the method comprising: providing a plurality of different target double-stranded polynucleotides; providing polynucleotide adapters, wherein each adapter comprises: (i) a double-stranded annealed region comprising complementarity between a first and second strand and wherein the second strand consists essentially of the region of complementarity and comprises a plurality of cleavable or excisable bases; and (ii) an overhang region on the first strand of the adapter; ligating the polynucleotide adapters to both ends of the different target double-stranded polynucleotides to form adapter-target constructs; subjecting the adapter-target constructs to conditions sufficient to cleave or excise the cleavable or excisable bases, thereby dissociating the second strand from the first strand of the adapters; and annealing an oligonucleotide to the first strand region of complementarity of the adapter-target constructs; thereby generating a library.

According to another aspect, there is provided a method for generating a library, the method comprising: providing a plurality of different target double-stranded polynucleotides; providing polynucleotide adapters, wherein each adapter comprises: (i) a double-stranded annealed region comprising complementarity between a first and second strand and wherein the second strand consists essentially of the region of complementarity; and (ii) an overhang region on the first strand of the adapter, and wherein said first strand comprises at least one cleavable or excisable bases; ligating the polynucleotide adapters to both ends of the different target double-stranded polynucleotides to form adapter-target constructs; denaturing the adapter-target constructs; annealing an oligonucleotide to the second strand region of complementarity of the denatured adapter-target constructs; extending the annealed oligonucleotide to produce extension products complementary to the adapter-target constructs; and subjecting the extension products and adapter-target constructs to conditions sufficient to cleave or excise the cleavable or excisable bases, thereby dissociating a 5' region of the first strand from the extension product; thereby generating a library.

The present invention in some embodiments thereof, is directed to a method for generating a library of different polynucleotide molecules, the method comprising: providing a plurality of different target double-stranded polynucleotides; providing identical polynucleotide adapters, wherein each adapter comprises: (i) a double-stranded annealed region comprising perfect complementarity between a first and second strand and wherein the second strand consists of the region of perfect complementarity; and (ii) an overhang region on the first strand of the adapter; ligating the double-stranded annealed regions of the identical polynucleotide adapters to both ends of the different target double-stranded polynucleotides to form adapter-target constructs; denaturing the adapter-target constructs; annealing an oligonucleotide to the second strand region of perfect complementarity of the denatured adapter-target constructs; and extending the annealed oligonucleotide to produce extension products complementary to the adapter-target constructs; thereby generating a library of different polynucleotide molecules.

As used herein, the term "oligonucleotide" refers to a short (e.g., no more than 100 bases), chemically synthesized single-stranded DNA or RNA molecule. In some embodiments, oligonucleotides are attached to the 5' or 3' end of a nucleic acid molecule, such as by means of ligation reaction. In some embodiments, the oligonucleotide is a primer. In some embodiments, the oligonucleotide is comprised on a solid support. In some embodiments, the oligonucleotide is attached to a solid support. In some embodiments, attached is linked. In some embodiments, linked is covalently linked. In some embodiments, the oligonucleotide is a first primer of a solid support.

In some embodiments, the adapter is the polynucleotide of the invention. In some embodiments, the adapter is a polynucleotide such as is described hereinabove. In some embodiments, the polynucleotide adapter, the identical polynucleotide adapters, or both, are the polynucleotide of the invention. In some embodiments, the polynucleotide adapters are all identical. In some embodiments, the regions of complementarity are perfectly complementary.

In some embodiments, 1, 2, 3, 4, 5, 6, 7, 8, 9, 10, 12, 14, 15, 16, 18, 19, 20, 22, 24, 25, 26, 28, 30, 32, 34, 36, 38, 40, 42 44, 45, 46, 48, or 50 adapters are provided. Each possibility represents a separate embodiment of the invention. In some embodiments, 1, 2, 3, 4, 5, 6, 7, 8, 9, 10, 12, 14, 15, 16, 18, 19, 20, 22, 24, 25, 26, 28, 30, 32, 34, 36, 38, 40, 42 44, 45, 46, 48, or 50 types of adapters are provided. Each possibility represents a separate embodiment of the invention. As used herein, a "type of adapter" refers to an adapter with a specific sequence. As such, two types of adapters will comprise at least one difference in their nucleotide sequence. In some embodiments, a single adapter is provided. In some embodiments, one type of adapters is provided. In some embodiments, one type of identical adapters is provided. In some embodiments, a plurality of adapters is provided.

In some embodiments, each adapter or each type of adapter comprises a different complementary region. In some embodiments, each adapter or each type of adapter comprises an identical overhang region. In some embodiments, each adapter or each type of adapter comprises a different barcode. In some embodiments, each adapter or each type of adapter is not complementary to another adapter or type of adapter. In some embodiments, each adapter or each type of adapter is devoid of a region of complementarity to another adapter or type of adapter. In some embodiments, each adapter or each type of adapter comprises less than 50, 45, 40, 35, 30, 25, 20, 15, 10, 5, 3, 2, or 1% complementarity to another adapter or type of adapter. Each possibility represents a separate embodiment of the invention.

In some embodiments, the adaptors comprise different barcodes. In some embodiments, the adaptors comprise different UMIs. In some embodiments, the method of the invention provides substantially less self-annealed target polynucleotides at the denaturation/annealing step. In some embodiments, substantially is at least 5% less, at least 10% less, at least 20% less, at least 30% less, at least 50% less, at least 70% less, or at least 90% less compared to control, or any value and range therebetween. Each possibility represents a separate embodiment of the invention. As used herein, the term "control" encompasses any ligation reaction product wherein at least 50%, at least 60%, at least 70%, or at least 80% of the ligation product comprises an identical double stranded region in both ends of a target polynucleotide.

It will be appreciated by a skilled artisan, that a different barcode or annealed region at the 5' end and 3' end of the adapter target complex will reduce self-complementarity. When only a single adapter type is introduced the adapter at the 5' end will be complementary to the adapter at the 3' end and this will cause self-annealing. The terms, "self-complementarity", "self-annealing" and "auto-hairpin formation" all refer to the binding of one region of the target-adapter complex to another region of the same target-adapter complex. In some embodiments, the self-complementarity can lead to formation of long chains of target-adapter complexes binding one to another. That is a region on one molecule can bind the complementary region on another molecule and so on, leading to formation of a chain. These types of non-primer binding (auto-annealing and chain formation) have negative impacts on PCR progression.

In some embodiments, the extension products comprise from 5' to 3': the overhang region, the first strand region of complementarity, the target polynucleotide, a reverse of the second strand region of complementarity and a reverse-complement of the overhang region. In some embodiments, the extension products comprise from 5' to 3': the oligonucleotide, a reverse complement of the target polynucleotide, the second strand region of complementarity and a reverse-complement of the overhang region. In some embodiments, the extension products comprise from 5' to 3': the 5' end of the oligonucleotide, a reverse complement of the second strand region of complementarity, a reverse complement of the target polynucleotide, the second strand region of complementarity and a reverse-complement of the overhang region.

Figure 2:
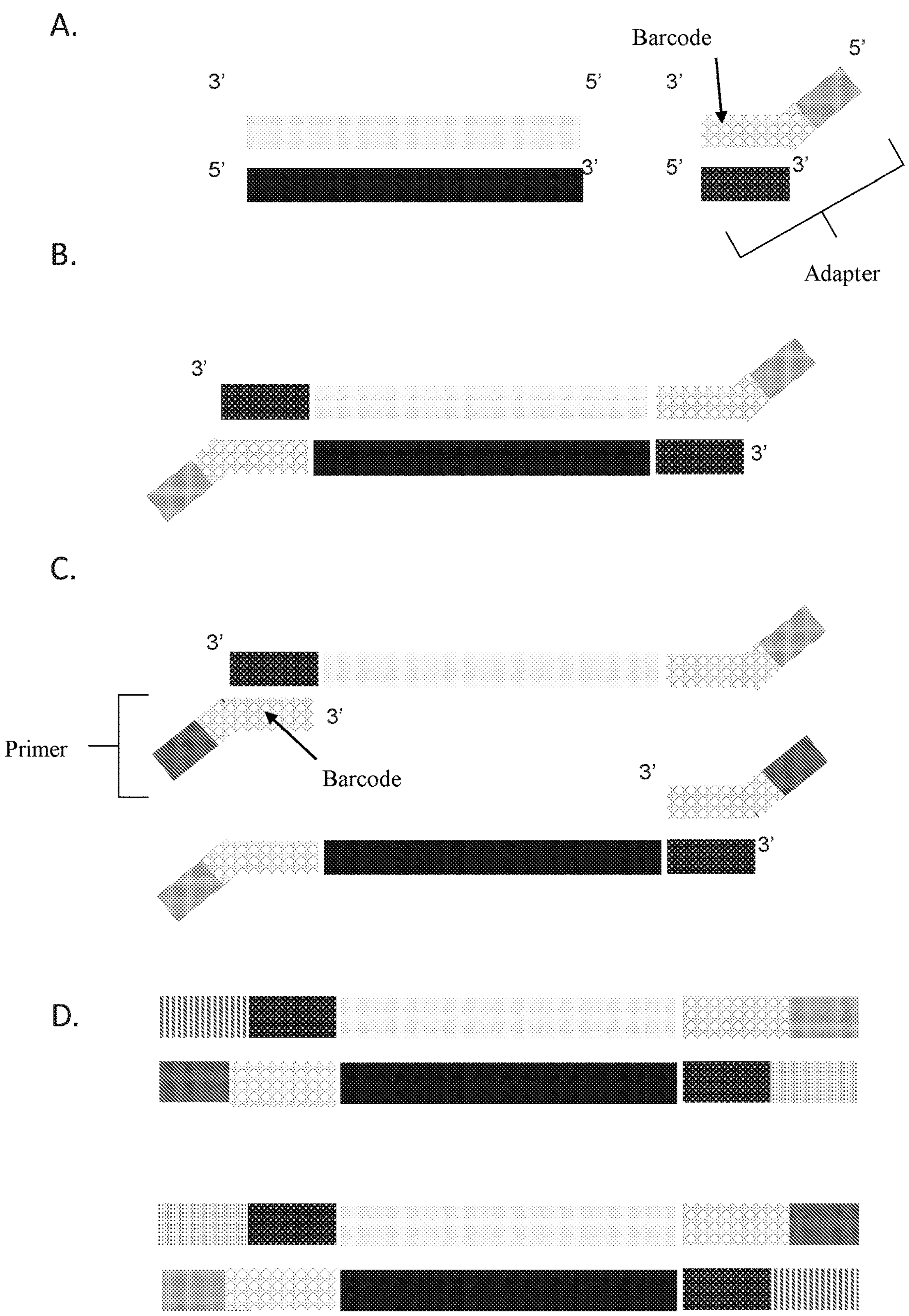
FIGS. 2A-2D are a step-by-step diagram of an embodiment of a method of the invention using primers with an overhang.

As can be seen in FIG. 2, a polynucleotide of the invention (the adapter) is introduced to a target polynucleotide duplex (2A). A single polynucleotide duplex is shown for simplicity. In some embodiments, the annealed region comprises a barcode. The barcode may be found in the first strand or the second strand. Optionally, the barcode may be found in an overhang region. In some embodiments, the overhang region comprises a region of a first primer (primer 1). In some embodiments, the overhang comprises a region that is complementary to a first primer. In some embodiments, the overhang comprises a region than can anneal to a first primer. In some embodiments, the first primer is a sequencing primer. In some embodiments, the overhang region is identical to a first primer. In some embodiments, the overhang region is homologous to a first primer. In some embodiments, the overhang region is identical or homologous to a first primer. In some embodiments, the first primer is on a solid support. In some embodiments, the first primer is the oligonucleotide.

A ligation is carried out, and an adapter is ligated to each end of each duplex (2B). Due to the presence of free phosphates, the 3' end of a strand of the adapter will ligate to a 5' end of a strand of the duplex. In some embodiments, the polynucleotide duplex is a double-stranded polynucleotide. In some embodiments, the 3' end of the first strand ligates to a 5' end of a strand of the different target double-stranded polynucleotides. In some embodiments, the 3' end of the first strand ligates to both 5' ends of a target double-stranded polynucleotide. In some embodiments, the 3' end of a first strand ligates to a 5' end of a first strand of the different target double-stranded polynucleotide and the 3' end of another first strand ligates to a 5' end of a second strand of the same target double-stranded polynucleotide. The ligation is performed using a suitable ligase enzyme (e.g., T4 DNA ligase) which joins two copies of the adapter to each DNA fragment, one at either end, to form adapter-target constructs. The products of this reaction can be purified from un-ligated adapter by a number of means, including size-inclusion chromatography, preferably by electrophoresis through an agarose gel slab followed by excision of a portion of the agarose that contains the DNA greater in size that the size of the adapter or any method known in the art.

"Ligation" of adapters to 5' and 3' ends of each target polynucleotide involves joining of the two polynucleotide strands of the adapter to double-stranded target polynucleotide such that covalent linkages are formed between both strands of the two double-stranded molecules. In this context "joining" means covalent linkage of two polynucleotide strands which were not previously covalently linked. Preferably such "joining" will take place by formation of a phosphodiester linkage between the two polynucleotide strands but other means of covalent linkage (e.g., non-phosphodiester backbone linkages) may be used. However, it is an essential requirement that the covalent linkages formed in the ligation reactions allow for read-through of a polymerase, such that the resultant construct can be copied in a primer extension reaction using primers which binding to sequences in the regions of the adapter-target construct that are derived from the adapter molecules.

The ligation reactions will preferably be enzyme-catalyzed. The nature of the ligase enzyme used for enzymatic ligation is not particularly limited. Non-enzymatic ligation techniques (e.g., chemical ligation) may also be used, provided that the non-enzymatic ligation leads to the formation of a covalent linkage which allows read-through of a polymerase, such that the resultant construct can be copied in a primer extension reaction.

The desired products of the ligation reaction are adapter-target constructs in which identical adapters are ligated at both ends of each target polynucleotide, given the structure adapter-target-adapter. Conditions of the ligation reaction should therefore be optimized to maximize the formation of this product, in preference to targets having an adapter at one end only.

The products of the ligation reaction may be subjected to purification steps in order to remove unbound adapter molecules before the adapter-target constructs are processed further. Any suitable technique may be used to remove excess unbound adapters, preferred examples of which will be described in further detail below.

In some embodiments, the adapter is removed. In some embodiments, the method is devoid of a step removing the adapter. Un-ligated target DNA remains in addition to ligated adapter-target constructs and this can be removed by selectively capturing only those target DNA molecules that have adapter attached. In embodiments wherein a biotin group is present on the free end of the overhang of the adapter, any target DNA ligated to the adapter can be captured on a surface coated with streptavidin, a protein that selectively and tightly binds biotin. Streptavidin can be coated onto a surface by means known to those skilled in the art. Biotin-streptavidin is but one capture option, and any such capture/purification system may be employed. In some embodiments, magnetic beads that are coated in streptavidin can be used to capture ligated adapter-target constructs. The application of a magnet to the side of a tube containing these beads immobilizes them such that they can be washed free of the un-ligated target DNA molecules.

With or without purification, the two strands can be separated in a denaturing step, or alternatively PCR or extension can be performed without a denaturing. Denaturing will improve the efficiency of the reaction. There are several standard methods for separating the strand of a DNA duplex by denaturation, including thermal denaturation, or chemical denaturation such as in 100 mM sodium hydroxide solution. The pH of a solution of single-stranded DNA in a sodium hydroxide collected from the supernatant of a suspension of magnetic beads can be neutralized by adjusting with an appropriate solution of acid, or preferably by buffer-exchange through a size-exclusion chromatography column pre-equilibrated in a buffered solution.

Figure 3:
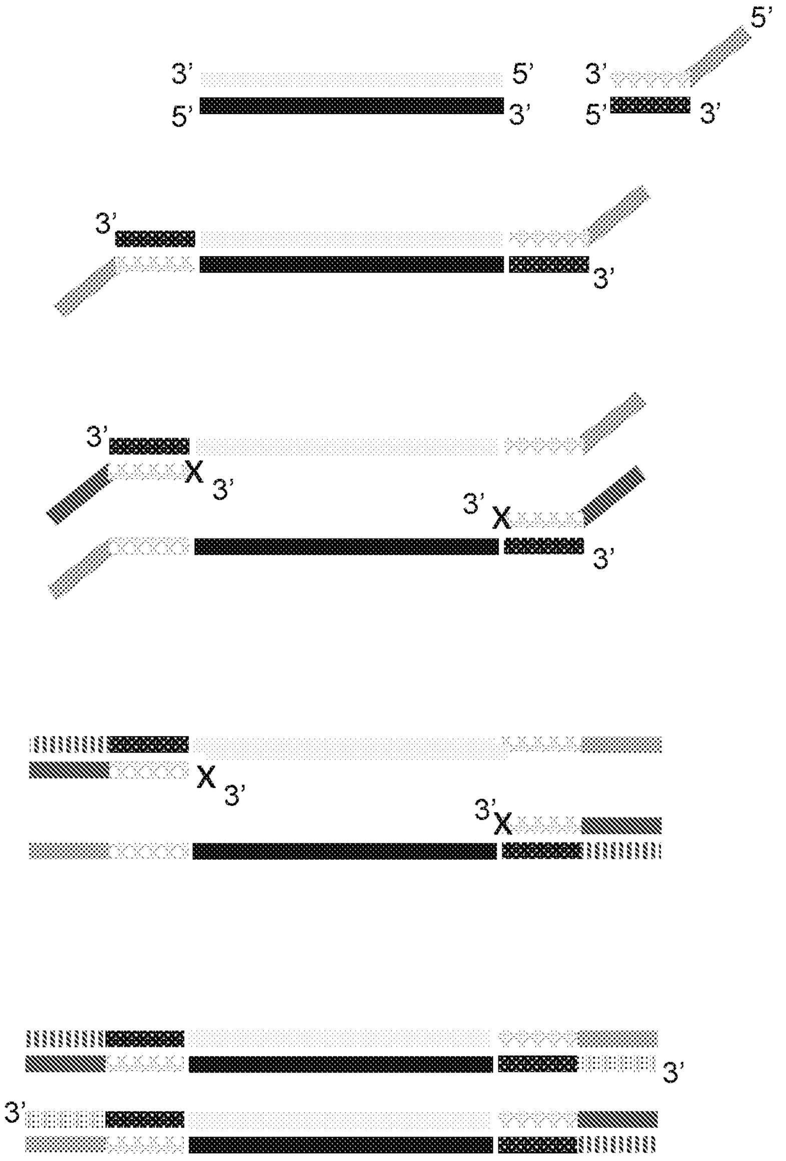
FIG. 3 is a step-by-step diagram of an embodiment of a method of the invention using non-extendable primers with an overhang.
Figure 4:
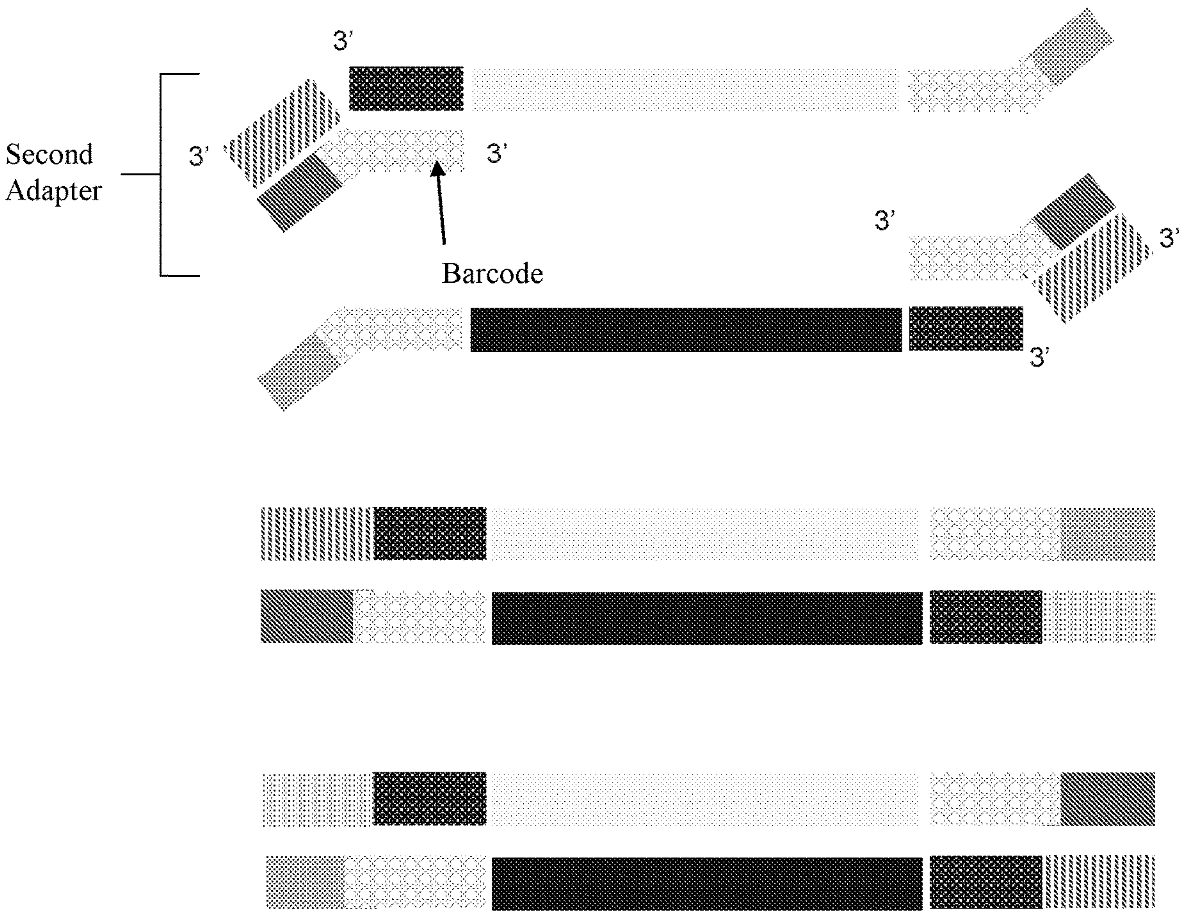
FIG. 4 is a step-by-step diagram of an embodiment of a method of the invention using a second adapter in place of a primer.

An oligonucleotide is administered to the denatured (or duplex) ligation products and an initial extension reaction is performed. The oligonucleotide can be a single strand primer (2C), a blocked/unextendible primer (FIG. 3) or a second double strand polynucleotide, i.e. a second adapter (FIG. 4). The use of blocked primers allows for the addition of as many new sequences as are desired. These additional sequences can be binding sites, cleavage sites, barcodes/UMIs or any sequence desired. This oligonucleotide is used as a template for an extension reaction. The polymerase in the extension reaction will extend from all free 3' ends that have a template for extension. This produces two double strand elongated molecules, each with the target duplex polynucleotide flanked by different sequences at the 5' and 3' ends (2D and FIG. 3-4). In some embodiments, the extension is PCR. In some embodiments, the extension comprises addition of reagents required for extension. Reagents may include, buffer, the polymerase, ions and/or free oligonucleotides. In some embodiments, at least a portion of the oligonucleotides are cleavable or excisable bases. In some embodiments, the oligonucleotides comprise uracil and are devoid of thymidine. In some embodiments, the oligonucleotides are DNA oligonucleotides and are devoid of one base and further comprise an RNA oligonucleotide of the missing base. In some embodiments, the base is selected from A, T, C, and G. In some embodiments, a missing T DNA base is replaced by an RNA U base.

The use of a second adapter is advantageous as it reduces template dependent hairpin formation. In the case that a second adapter is used, the second adaptor comprises an alternative double stranded region that is different from that of the first adapter. The double stranded region may serve as UMI or generally as a barcode. In the case that the same double strand is present in the polynucleotide of the invention and in the herein disclosed adaptor, an intra molecular hairpin may form thereby competing with the inter molecular primer binding. Therefore, using a polynucleotide and an adaptor having different double stranded regions, e.g., harboring numerous barcodes or UMIs, the probability of hairpin formation is statistically and significantly reduced (depending on pool size). Further, by having different UMIs/barcodes at each end allows for greater multiplexing and higher levels of labeling. For example, 20 or so double strand sequences, provides about 20×20 options for UMIs when ligation is on both ends.

In some embodiments, the oligonucleotide comprises a 3' region homologous or identical to the annealed region of the first strand of the polynucleotide of the invention. In some embodiments, the oligonucleotide comprises a 5' region comprises a sequence not found in the polynucleotide of the invention. In some embodiments, the 5' region comprises a sequence different than the overhang of the first strand. In some embodiments, the oligonucleotide further comprises a capture moiety. In some embodiments, the capture moiety is different than the capture moiety of the polynucleotide. In some embodiments, the 5' region comprises the capture moiety. In some embodiments, the capture moiety is at a 5' end of the 5' region. In some embodiments, the oligonucleotide further comprises at least one cleavable or excisable base. In some embodiments, the 5' region of the oligonucleotide comprises at least one cleavable or excisable base. In some embodiments, the oligonucleotide further comprises a plurality of cleavable or excisable base. In some embodiments, the 5' region of the oligonucleotide comprises a plurality of cleavable or excisable base. In some embodiments, the oligonucleotide comprises a capture moiety and at least one cleavable or excisable base configured such that excision of the cleavable or excisable base results in dissociation of the capture moiety from the oligonucleotide. In some embodiments, the cleavable or excisable base is proximal to the capture moiety. In some embodiments, the capture moiety is 5' to the cleavable or excisable base. In some embodiments, the cleavable or excisable base is 3' to the capture moiety. In some embodiments, cleavage of the cleavable or excisable base from the oligonucleotide results in loss of the capture moiety from the oligonucleotide. In some embodiments, the oligonucleotide comprises a sufficient number of cleavable bases, sufficiently close to each other, such that excision of the cleavable bases induces dissociation of the non-complementary 5' end from a reverse complement of the non-complementary 5' end.

In some embodiment a capture moiety is at a 5' end of a strand or oligonucleotide. In some embodiments, a capture moiety is at a 3' end of a strand or oligonucleotide. In some embodiments, a cleavable or excisable base is proximal to a capture moiety. In some embodiments, excision or cleavage of the cleavable or excisable base results is dissociation of the capture moiety from the strand or oligonucleotide. It will be appreciated by a skilled artisan that a capture moiety, such as biotin, can be attached to a 5' end of a nucleic acid molecule, in particular the most 5' base can be biotinylated. Similarly, that 5' base could also be a cleavable or excisable base and so its removal will inherently remove the biotin. Alternatively, the cleavable base could be proximal though not at the biotinylated base, but removal of the cleavable base would render the intervening bases between the gap/nick/hole and the biotinylated base unstable such that all the bases would dissociate. If the oligonucleotide bearing the biotin is single stranded, and does not have a synthesizes complement (which occurs if the opposite strand has a 3' block, see for example FIG. 5) than any cleavage along the single strand will result in dissociation of a 5' biotinylated base.

The term "initial" extension reaction refers to a primer/adapter extension reaction in which primers/adapters are annealed directly to the adapter-target constructs, as opposed to either complementary strands formed by primer extension using the adapter-target construct as a template or amplified copies of the adapter-target construct. A universal primer/adapter is used and not a target-specific primer or a mixture of random primers. The use of an adapter-specific primer for the initial primer extension reaction is key to formation of a library of templates which have common sequence at the 5' and common sequence at the 3' end.

The primers/adapters used for the initial primer extension reaction will be capable of annealing to each individual strand of adapter-target constructs having adapters ligated at both ends and can be extended so as to obtain two separate primer extension products, one complementary to each strand of the construct. Thus, in the most preferred embodiment the initial primer extension reaction will result in formation of primer extension products complementary to each strand of each adapter-target.

In some embodiments, the extension products comprise from 5' to 3': (a) (i) the overhang region and the first strand region of complementarity of a first adaptor; (ii) the target polynucleotide; (iii) the second strand region of complementarity of a second adaptor; and (iv) a reverse-complement of an overhang of the oligonucleotide, wherein the overhang extends from the region of complementarity of the oligonucleotide and the denatured adapter-target construct; (b) (i) the oligonucleotide (ii) the target polynucleotide or a reverse complement thereof; and (iii) a reverse-complement of the first strand region of complementarity and the overhang region of the first adaptor; or any combination thereof. In some embodiments, the extension products comprise from 5' to 3': (i) the oligonucleotide (ii) the target polynucleotide or a reverse complement thereof; and (iii) a reverse-complement of the first strand region of complementarity and the overhang region of the first adaptor. In some embodiments, the extension products comprise from 5' to 3': (i) the overhang region of the oligonucleotide (ii) the first strand region of complementarity or a homolog thereof; (iii) the target polynucleotide or a reverse complement thereof; and (iv) a reverse-complement of the first strand. In some embodiments, the first and second adaptors are identical. In some embodiments, the first and second adapters are different.

In one embodiment the primer/adapter used in the initial primer extension reaction will anneal to a primer-binding sequence (in one strand) in the annealed region of the adapter. In some embodiments, the primer-binding sequence is in the first strand of the first adapter. In some embodiments, the primer-binding sequence is in the second strand of the first adapter. In some embodiments, the primer-binding sequence is a portion of the region of complementarity of the second strand. In some embodiments, the primer-binding sequence is the region of complementarity of the second strand.

In some embodiments, the method of the invention is "PCR-free". As used herein, the term "PCR-free" refers to that the method is devoid of a step comprising exponential amplification of a polynucleotide template using a set of primers and a polymerizing enzyme. In some embodiments, the extension step does comprise amplification.

In some embodiments, the method comprises an amplification protocol comprising a limited number of amplification cycles. In some embodiments, the term "limited" comprises 1 to 6 amplification cycles, 1 to 5 amplification cycles, 1 to 4 amplification cycles, 2 to 6 amplification cycles, 3 to 5 amplification cycles, 4 to 6 amplification cycles, 2 to 5 amplification cycles, or 3 to 6 amplification cycles, using PCR, or any value and range therebetween. Each possibility represents a separate embodiment of the invention. In some embodiments, limited is less than 2, 3, 4, 5, 6, 7, 8, 9, or 10 amplification cycles. Each possibility represents a separate embodiment of the invention.

Figure 5:
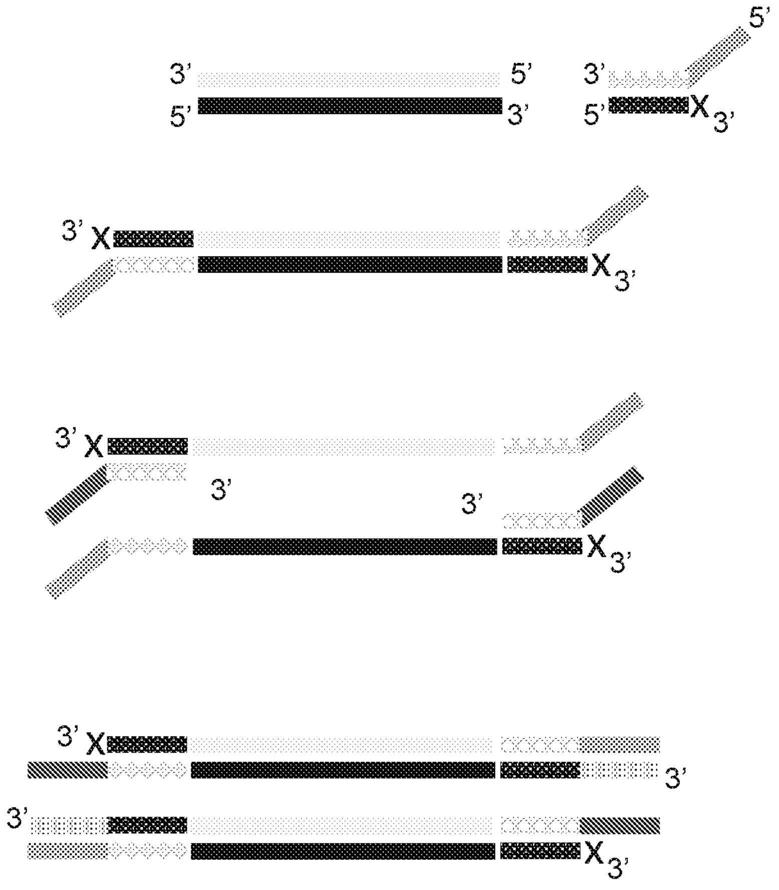
FIG. 5 is a step-by-step diagram of an embodiment of a method of the invention using a second adapter blocked at 3' end in place of a primer.
Figure 6:
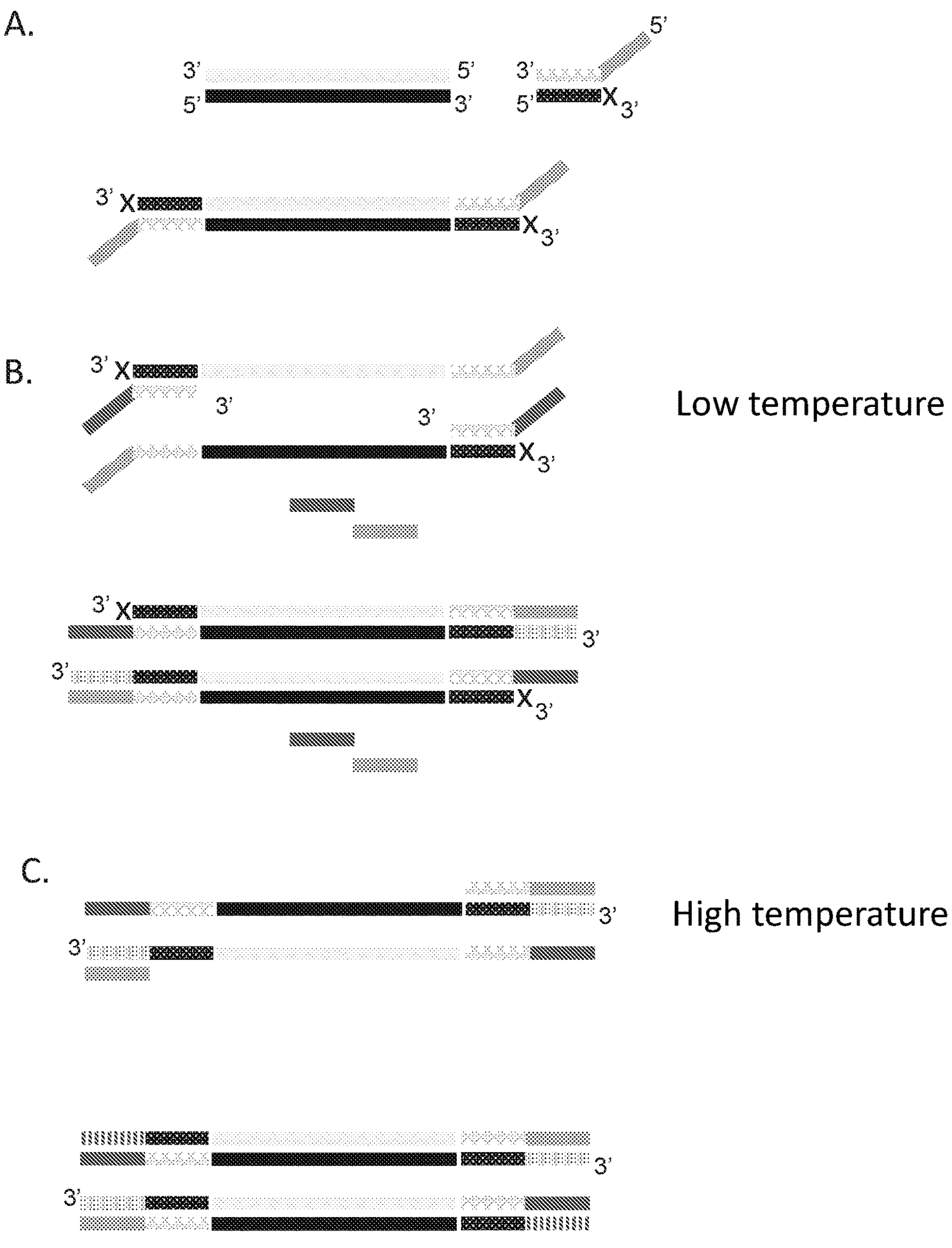
FIGS. 6A-6C are a step-by-step diagram of an embodiment of a method of the invention using a blocked second adapter with PCR cycles at different temperatures.

As seen in FIG. 5, the 3' end of the second strand of the adapter can also be the blocked/non-extendable end. In this configuration the complementary, newly transcribed, strands become full strands. Additionally, this configurating can be made more effective by first running PCR cycles at a low annealing temperature. This will favor binding of the complementary region of the primer to one of the blocked strands even though no overhang will bind (FIG. 6A). Several rounds of PCR can be run at this lower temperature (FIG. 6B). Subsequently, PCR cycles can be run at a higher temperature that will favor binding of the entire primer including the "overhang" region (FIG. 6C). This will favor binding to the full-length transcripts.

In some embodiments, the amplification protocol comprises amplification cycles having different annealing temperatures. In some embodiments, the amplification protocol comprises at least 2 different annealing temperatures. In some embodiments, the first annealing temperate is at least 1° C., at least 2° C., at least 3° C., at least 4° C., at least 5° C., at least 7° C., or at least 10° C. greater than the second annealing temperature, or any value and range therebetween. Each possibility represents a separate embodiment of the invention. In some embodiments, the second annealing temperate is at least 1° C., at least 2° C., at least 3° C., at least 4° C., at least 5° C., at least 7° C., or at least 10° C. greater than the first annealing temperature, or any value and range therebetween. Each possibility represents a separate embodiment of the invention.

In some embodiments, the annealing temperature increases gradually or decreases gradually with each amplification round. In some embodiments, gradually comprises at least ±0.5° C. or at least ±1° C. per amplification round. Each possibility represents a separate embodiment of the invention.

It will be understood by a skilled artisan, that binding by a longer sequence will be favored at a higher annealing temperature and binding by a shorter sequence will be favored at a lower temperature. Thus, by altering the annealing temperature the annealing can be pushed toward binding of just the double-strand complementary region of the primer or adapter (lower temperature) or toward binding of the entire primer or adapter including the overhang (higher temperature). This difference can be exacerbated by designing overhang regions with relatively high melting temperatures, or complementary/annealed/double strand regions with relatively low melting temperatures.

The primer comprises an overhang region that is not complementary to any sequence in the adapter-target molecule. Upon PCR a complement to this region will be extended from the 3' end of the adapter-target molecule. In embodiments using a second adapter, this region is already annealed as part of the second adapter. In some embodiments, the overhang region of the primer is identical to the overhang region of the first adapter. In some embodiments, the overhang region of the primer is different to the overhang region of the first adapter.

In some embodiments, the primer comprises a region complementary to the second strand of the polynucleotide adapter. In some embodiments, the primer comprises a region that anneals to the second strand of the polynucleotide adapter. In some embodiments, the region that is complementary or anneals is the 3' end of the primer. In some embodiments, the annealed region or complementary region of the primer is the same as the annealed region of the first strand of the adapter. In some embodiments, the annealed region or complementary region of the primer is the substantially the same as the annealed region of the first strand of the adapter. In some embodiments, the annealed region or complementary region of the primer is at least 80, 85, 90, 95, 97, 98, 99 or 100% identical to the annealed region of the first strand of the adapter. In some embodiments, the annealed region or complementary region of the primer comprises a barcode.

In some embodiments, the 5' end of the primer overhangs the ligation product. In some embodiments, the primer comprises an overhang region. In some embodiments, the overhang region of the primer is different from the overhang region of the first strand of the adapter. In some embodiments, the overhang region of the primer is the same as the overhang region of the first strand of the adapter. In some embodiments, the overhang region is substantially different from the overhang region of the first strand of the adapter. In some embodiments, the overhang region comprises a second primer (primer 2). In some embodiments, the overhang region comprises a region complementary to a second primer. In some embodiments, the overhang region comprises a region that can be annealed by a second primer. In some embodiments, the second primer is a sequencing primer. In some embodiments, the first and second primers are the same.

Figure 7A:
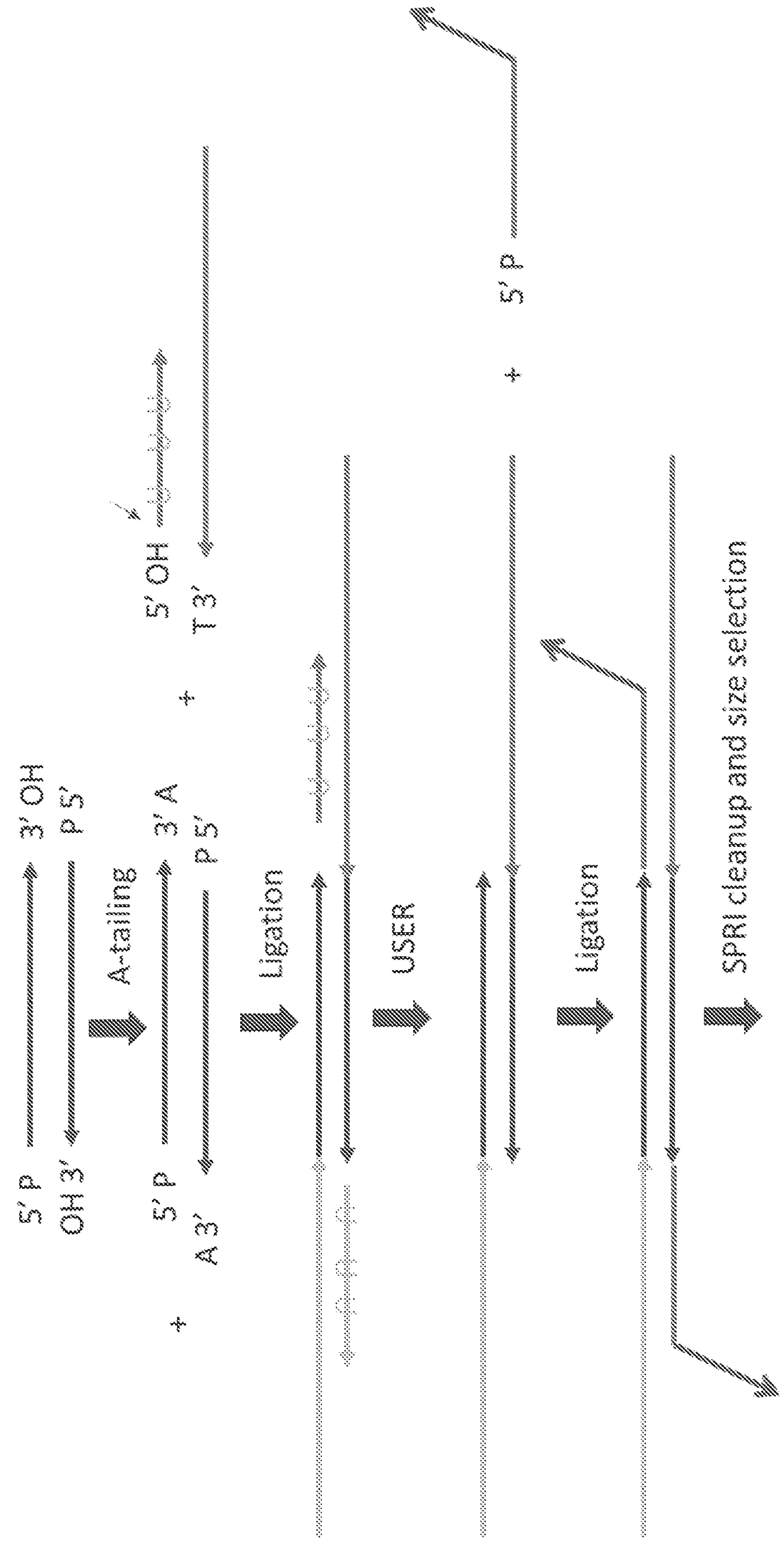
FIGS. 7A-7B are a step-by-step diagram of (7A) an embodiment of a method of the invention using adapters with cleavable bases in the second strand and (7B) the resultant degradation of adapter dimers.

In an alternative embodiment, when cleavable or excisable bases are included in the second strand of the adapters, instead of denaturing, the adapter-target constructs are subjected to conditions for excision of the excisable bases. This excision causes dissociation of the second strand of the adapters from the first strands of the adapters. After this dissociation an oligonucleotide can be annealed or hybridized to the first strand region of complementarity of the adapter-target constructs (FIG. 7A). The oligonucleotide can then be ligated in place by blunt end ligation. Alternatively, the nick can be filled in, such as with an exonuclease. As this method does not include dissociation of the strands and primer extension, the final result is only two total strands. In contrast, the method employing dissociation and extension produces four strands total.

In some embodiments, the conditions sufficient to cleave or excise the cleavable or excisable bases comprise brining the adapter-target constructs in contact with a cleaving agent. In some embodiments, the method further comprises adding a cleaving agent. In some embodiments, the method further comprises contacting the adapter-target with a cleaving agent. In some embodiments, the cleaving agent is selected from the group consisting of uracil DNA glycosylase (UDG), apyrimidinic/apurinic endonuclease (APE), endonucleases (e.g., endonuclease VIII (EndoVIII) or V (EndoV)), uracil-specific excision reagent (USER™) enzyme (a mixture of UDG and endonuclease VIII), formamidopyrimidine DNA glycosylase (Fpg), 8-oxoguanine glycosylase (OGG1), RNase (e.g., RNaseH, such as RNaseHII), ultraviolet light, and a combination thereof. FIG. 7A shows a specific embodiment in which the cleavable base is a uracil RNA base within a DNA backbone and the cleaving agent is USER™ (a mixture of UDG and endonuclease VIII).

Figure 7B:
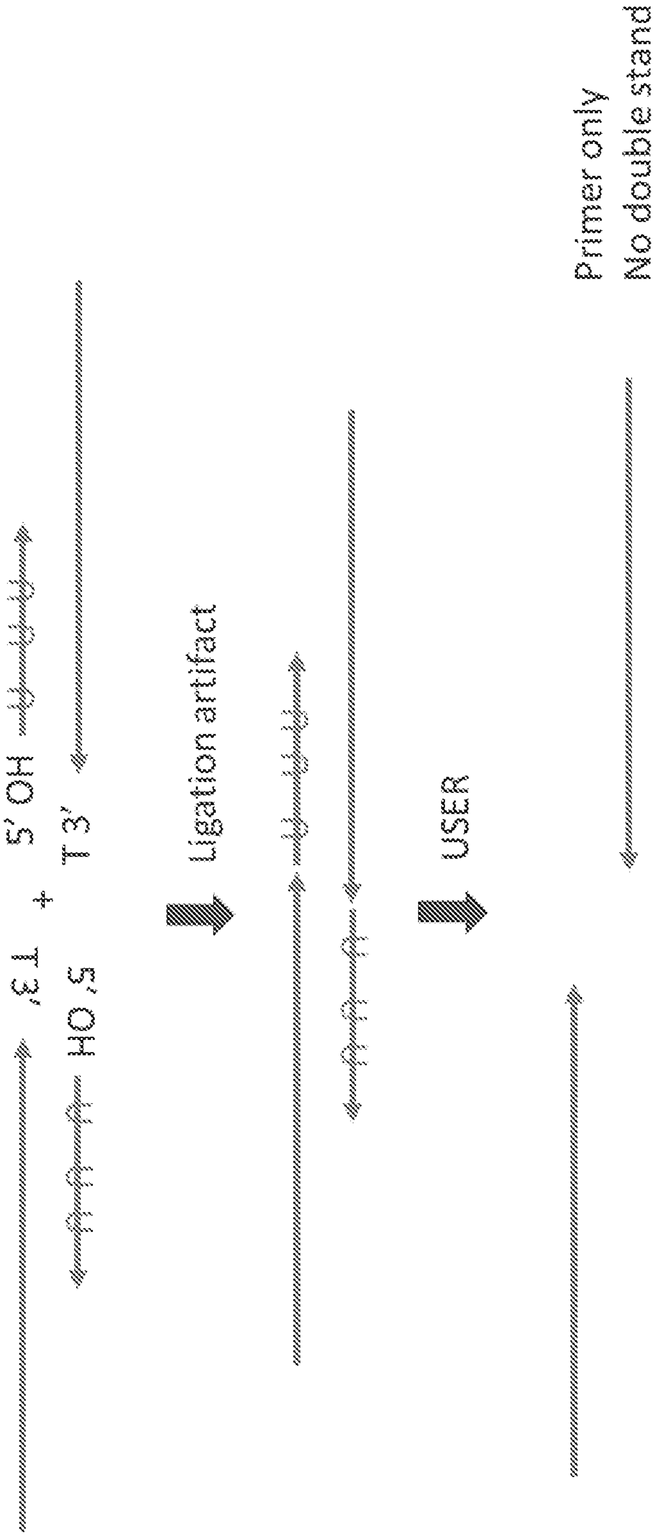

In some embodiments, step (d) further comprises subjecting an adapter dimer produced in step (c) to the conditions sufficient to cleave or excise the cleavable or excisable bases, thereby degrading the adapter dimers. In some embodiments, the subjecting further comprises subjecting an adapter dimer produced by the ligating to the conditions sufficient to cleave or excise cleavable or excisable bases, thereby degrading the adapter dimers. A skilled artisan will appreciate that adapter dimers will form in blunt end or T/A overhang ligations. The removal of a phosphate from one end of the adapter will decrease the chance of dimers, but dimers will nevertheless form. Indeed, adapter dimers are unavoidable with all methods currently known in the art. And these contaminants make later steps more difficult and often end up producing thousands of sequencing reads that are empty (i.e. just adapters). Further, the tendency to form dimers forces the use of lower concentrations of adapters. Using too high a concentration leads to a great excess of dimers and a loss of much reagent. Currently standard library preparations call for a maximum molar ratio of 200:1 adapter to insert. This is a maximum and indeed many preparations a run at much lower ratios, even as low as 10:1. In the method described herein, the adapter dimers will all contain cleavable based, and excision of these cleavable bases will degrade both second strands found in the dimer and cause the dimer to dissociate, leaving only single-stranded DNA that can be easily removed (FIG. 7B). This allows the use of much higher concentrations of adapters without the adverse side effect of adapter dimers. In some embodiments, the adapters are greatly in excess of the different target double-stranded polynucleotides. In some embodiments, the adapters are provided in a concentration greatly in excess. In some embodiments, greatly in excess is as compared to a method of library preparation in which the adapters do not comprise cleavable or excisable bases. In some embodiments, greatly in excess is as compared to a method of library preparation other than a method of the invention. In some embodiments, greatly in excess is as compared to standard protocols. In some embodiments, greatly in excess is at a molar ratio of more than 200:1. In some embodiments, greatly in excess is at a molar ratio of more than 100:1, 150:1, 200:1, 250:1, 300:1, 350:1, 400:1, 450:1, 500:1, 600:1, 700:1, 800:1, 900:1, or 1000:1. Each possibility represents a separate embodiment of the invention. This aspect also allows for a process that does not include removing excess adapters, as the adapters will be digested, and single strand molecules can be easily removed.

In some embodiments, the target polynucleotide duplexes are selected from: genomic DNA or a fragment thereof, cell-free DNA, cDNA, RNA, or double stranded RNA. In some embodiments, the target polynucleotide duplexes are a plurality of target DNA molecules having different sequences. In some embodiments, the target polynucleotides are blunt ended. In some embodiments, the method further comprises blunting the ends of the target polynucleotides.

The one or more "target polynucleotide duplexes" or "target double-stranded polynucleotides" to which the adapters are ligated may be any polynucleotide molecules that it is desired to amplify by solid-phase PCR, generally with a view to sequencing. The target polynucleotide duplexes may originate in double-stranded DNA form (e.g., genomic DNA fragments) or may have originated in single-stranded form, as DNA or RNA, and been converted to dsDNA form prior to ligation. By way of example, mRNA molecules may be copied into double-stranded cDNAs suitable for use in the method of the invention using standard techniques well known in the art. The precise sequence of the target molecules is generally not material to the invention and may be known or unknown. Modified DNA molecules including non-natural nucleotides and/or non-natural backbone linkages could serve as the target, provided that the modifications do not preclude adapter ligation and/or copying in a primer extension reaction.

Although the method could in theory be applied to a single target duplex (i.e. one individual double-stranded molecule), it is preferred to use a mixture or plurality of target polynucleotide duplexes. The method of the invention may be applied to multiple copies of the same target molecule (so-called mono-template applications) or to a mixture of different target molecules which differ from each other with respect to nucleotide sequence over all or a part of their length, e.g., a complex mixture of templates. The method may be applied to a plurality of target molecules derived from a common source, for example a library of genomic DNA fragments derived from a particular individual. In a preferred embodiment the target polynucleotides will comprise random fragments of human genomic DNA. The fragments may be derived from a whole genome or from part of a genome (e.g., a single chromosome or sub-fraction thereof), and from one individual or several individuals. The DNA target molecules may be treated chemically or enzymatically either prior to, or subsequent to the ligation of the adaptor sequences. Techniques for fragmentation of genomic DNA include, for example, enzymatic digestion or mechanical shearing.

The target polynucleotides may be generated with blunt ends or blunt ends may be added. For example, fragmented DNA may be made blunt-ended by a number of methods known to those skilled in the art. In some embodiments, the ends of the fragmented DNA are end repaired with T4 DNA polymerase and Klenow polymerase, a procedure well known to those skilled in the art, and then phosphorylated with a polynucleotide kinase enzyme.

In some embodiments, the target polynucleotide duplexes are or represent a total cell genome, a total cell transcriptome (either RNA, or reverse transcribed cDNA). In some embodiments, the target polynucleotide duplexes are a pool of polynucleotide molecules obtained from: different cells of the same organism, different organisms of the same species, different species, different developmental stages of the same species, or any combination thereof.

According to the herein disclosed method, in some embodiments thereof, two copies of any target polynucleotide duplex are produced. In some embodiments, the target polynucleotide is from the plurality of target polynucleotides. In some embodiments, a double stranded target polynucleotide is a target polynucleotide duplex. In some embodiments, a single copy of any target double-stranded polynucleotide is produced. In some embodiments, in the two copies different strands comprise a region complementary to primer 1. In some embodiments, in the two copies different strands comprise a region complementary to primer 2. In some embodiments, in the two copies different strands comprise primer 1. In some embodiments, in the two copies different strands comprise primer 2. In some embodiments, all 4 strands in the two copies comprise a region complementary to primer 1. In some embodiments, all 4 strands in the two copies comprise a region complementary to primer 2. In some embodiments, all 4 strands of the two copies comprise primer 1. In some embodiments, all 4 strands of the two copies comprise primer 2.

In some embodiments, the oligonucleotide comprises a 5' end that is not complementary to the second strand region of perfect complementarity and the extending further comprises extending from a 3' end of the adapter-target constructs to generate a 3' region complementary to the non-complementary 5' end of the oligonucleotide. In some embodiments, all 3' ends are extended. In some embodiments, a single round of PCR is performed. In some embodiments, multiple rounds of PCR are performed. In some embodiments, a method for preparing a chimeric DNA molecule, comprising ligating the polynucleotide of the invention to a double stranded DNA molecule, thereby preparing a chimeric DNA molecule, is provided. In some embodiments, the target double stranded DNA molecule comprises blunt ends.

In some embodiments, blunt ends comprise all blunt ends.

In some embodiments, the method further comprises the steps of denaturing the chimeric DNA molecule and annealing a single stranded DNA oligonucleotide to the annealed portion within a single stranded DNA molecule of the chimeric DNA molecule (SSCDM), to obtain the SSCDM annealed to the single stranded DNA oligonucleotide.

In some embodiments, the single stranded DNA oligonucleotide comprises a nucleic acid sequence complementary to the annealed portion of the polynucleotide of the invention. In some embodiments, the single stranded DNA oligonucleotide comprises a nucleic acid sequence complementary to a segment of the polynucleotide of the invention.

As used herein, the term "segment" refers to at least 50%, at least 60%, at least 70%, at least 80%, at least 90%, or at least 95% of the polynucleotide of the invention, or any value and range therebetween. Each possibility represents a separate embodiment of the invention. In some embodiments, the segment is 99% of the polynucleotide of the invention, at most.

In some embodiments, the single stranded DNA oligonucleotide annealed to the 3'-end segment of the annealed portion comprises a 5'-end overhang.

In some embodiments, the single stranded DNA oligonucleotide consists 15 to 40 nucleotides, 10 to 30 nucleotides, 25 to 45 nucleotides, 12 to 35 nucleotides, 9 to 36 nucleotides, 8 to 50 nucleotides, 17 to 35 nucleotides, or 20 to 46 nucleotides. Each possibility represents a separate embodiment of the invention.

In some embodiments, the single stranded DNA oligonucleotide has a melting temperature ranging from 55 to 70° C. In some embodiments, the single stranded DNA oligonucleotide single stranded DNA oligonucleotide has a melting temperature of at least 55° C., at least 60° C., at least 65° C., at least 67° C., at least 70° C., or any value and range therebetween. Each possibility represents a separate embodiment of the invention.

In some embodiments, the single stranded DNA oligonucleotide has a G/C content ranging from 50% to 70%. In some embodiments, the single stranded DNA oligonucleotide has a G/C content of at least 50%, at least 60%, at least 65%, at least 70%, or any value and range therebetween. Each possibility represents a separate embodiment of the invention.

In some embodiments, the 5' end of the oligonucleotide is reverse complementary to the complementarity region of the adapter. In some embodiments, the 5' end of the oligonucleotide is reverse complementary to the complementarity region of the first strand of the adapter. In some embodiments, the 5' end of the oligonucleotide hybridizes or anneals to the complementarity region of the first strand of the adapter. In some embodiments, the oligonucleotide comprises a 3' region that is not complementary to the adapter. In some embodiments, the oligonucleotide comprises a 3' region this is not complementary to the first strand of the adapters. In some embodiments, the 3' region is the 3' end of the oligonucleotide. In some embodiments, the 5' region is the 5' end of the oligonucleotide. In some embodiments, the 5' region is upstream of the 3' region. In some embodiments, the method produces a library of different double-stranded polynucleotide molecules each comprising region of non-complementarity at a 5' end and a 3' end. Such library well known to be used in sequencing assays.

In some embodiments, the method further comprises extending SSCDM template annealed single stranded DNA oligonucleotide. In some embodiments, extending comprises extending the 3'-end of the single stranded DNA oligonucleotide annealed with the single stranded DNA molecule of the chimeric DNA molecule (SSCDM) based on the chimeric DNA molecule as a template, extending 3'-end of the single stranded DNA molecule of the chimeric DNA molecule annealed with the single stranded DNA oligonucleotide based on the single stranded DNA oligonucleotide as a template, or both. In some embodiments, the method further comprises amplifying an extension product by a polymerase chain reaction (PCR).

The conditions encountered during the annealing steps of a PCR reaction will be generally known to one skilled in the art, although the precise annealing conditions will vary from reaction to reaction (see Sambrook et al., 2001, *Molecular Cloning, A Laboratory Manual,* 3rd Ed, Cold Spring Harbor Laboratory Press, Cold Spring Harbor Laboratory Press, NY; Current Protocols, eds Ausubel et al.). Typically such conditions may comprise, but are not limited to, (following a denaturing step at a temperature of about 94° C. for about one minute) exposure to a temperature in the range of from 40° C. to 72° C. (preferably 50-68° C.) for a period of about 1 minute in standard PCR reaction buffer.

Different annealing conditions may be used for a single primer extension reaction not forming part of a PCR reaction (again see Sambrook et al., 2001, *Molecular Cloning, A Laboratory Manual,* 3rd Ed, Cold Spring Harbor Laboratory Press, Cold Spring Harbor Laboratory Press, NY; Current Protocols, eds Ausubel et al.). Conditions for primer annealing in a single primer extension include, for example, exposure to a temperature in the range of from 30 to 37° C. in standard primer extension buffer. It will be appreciated that different enzymes, and hence different reaction buffers, may be used for a single primer extension reaction as opposed to a PCR reaction. There is no requirement to use a thermostable polymerase for a single primer extension reaction.

The term "annealing" as used in this context refers to sequence-specific binding/hybridization of the primer to a primer-binding sequence in an adapter region of the adapter-target construct under the conditions to be used for the primer annealing step of the initial primer extension reaction.

The products of the primer extension reaction may be subjected to standard denaturing conditions in order to separate the extension products from strands of the adapter-target constructs. Optionally the strands of the adapter-target constructs may be removed at this stage. The extension products (with or without the original strands of the adapter-target constructs) collectively form a library of template polynucleotides which can be used as templates for PCR.

If desired, the initial primer extension reaction may be repeated one or more times, through rounds of primer annealing, extension and denaturation, in order to form multiple copies of the same extension products complementary to the adapter-target constructs.

The products of further PCR amplification may be collected to form a library of templates comprising "amplification products derived from" the initial primer extension products. In some embodiments, both primers used for further PCR amplification will anneal to different primer-binding sequences on opposite strands in the overhang region of the first adapter and the primer/second adapter. Other embodiments may, however, be based on the use of a single type of amplification primer which anneals to a primer-binding sequence in the double-stranded region of the adapter. In embodiments of the method based on PCR amplification the "initial" primer extension reaction occurs in the first cycle of PCR.

Inclusion of the initial primer extension step (and optionally further rounds of PCR amplification) to form complementary copies of the adapter-target constructs (prior to whole genome or solid-phase PCR) is advantageous, for several reasons. Firstly, inclusion of the primer extension step, and subsequent PCR amplification, acts as an enrichment step to select for adapter-target constructs with adapters ligated at both ends. Only target constructs with adapters ligated at both ends provide effective templates for whole genome or solid-phase PCR using common or universal primers specific for primer-binding sequences in the adapters, hence it is advantageous to produce a template library comprising only double-ligated targets prior to solid-phase or whole genome amplification.

In some embodiments, the PCR performed is emulsion PCR. In some embodiments, clonal copies of the adapter target constructs, or complementary copies thereof, are produced on solid support using emulsion PCR. Methods of performing emulsion PCR and producing clonal copies on solid supports can be found in U.S. Pat. No. 8,765,380 and International Patent Application WO2019079653, the contents of which are herein incorporated by reference. Methods of performing sequencing by synthesis on clonal populations can be found in at least U.S. Pat. Nos. 9,902,951 and 8,772,473, the contents of which are herein incorporated by reference.

In some embodiments, the method further comprises a pre-enrichment step. Pre-enrichment can be done before further enzymatic reactions. In some embodiments, pre-enrichment results in a solid support, i.e. a bead, with a template nucleic acid strand attached. Such pre-enrichment is particularly advantageous in enzymatic reactions such as emulsion PCR (emPCR) as the pre-attachment of template to bead improves clonal amplification of template nucleic acid molecules by avoiding wasted reagents and lost sample by circumventing the double-Poisson distribution problem inherent is clonal PCR. PCR amplification performed in partitions requires the distribution of nucleic acid templates and amplification beads to the various partitions. Standard amplification calls for a single bead and a single template to be present in a partition to facilitate the production of a clonal bead bound by amplification products homologous or complementary to the template nucleic acid. When a partition contains only a bead, only a nucleic acid, or neither no amplification can occur and the reagents in the partition are wasted. Further, precious nucleic acid templates with no bead are also lost. Partitions with more than one nucleic acid produce a polyclonal bead which cannot be properly analyzed also resulting in wasted reagents and template. For a given case of "N" number of nucleic acid molecules and "B" number of beads randomly distributed among partitions which are greatly in excess, the relative bead population found in partitions with any number of DNAs (0, 1 or >1 nucleic acid molecules) is dependent on the ratio of N/M. When beads and temple nucleic acids are distributed into partitions separately each will follow its own Poisson distribution leading to a double-Poisson problem. The fraction of beads containing N number of nucleic acids, R(N) may be calculated as:

$$R(N)=e\hat{}-(N/M)x(N/M)\hat{}N/N!$$

In order to maximize partitions with only one bead and only one nucleic acid template an N/M ratio of 1 would be selected. In such a case 37% of beads will be alone in a partition, 26% of beads will be in partitions with more than one template and 37% of beads will be in partitions with a single template. This is already a large loss of template. However, due to the double-Poisson issue the situation is even worse. Of those partitions with only a single template molecule some will have multiple beads, so the percentage of nucleic acids in partitions with a single bead is even less than 37%, and indeed approximately 22%. Similarly, only 22% of template molecules will be in partitions with a single bead and single template. With pre-enrichment, wherein complements to a template molecule are linked to the amplification bead, all beads have bound nucleic acids before distribution to the partitions thus removing one of the Poisson distributions.

In some embodiments, the method further comprises subjecting the generated library of different polynucleotide molecules to conditions sufficient to cleave or excise the cleavable or excisable bases, thereby dissociating the non-complementary 5' end from a second strand to produce a single-strand overhang library. In some embodiments, a single-strand overhang library is a cleaved library. In some embodiments, the method further comprises contacting the single-strand overhang library with a plurality of enrichment solid supports. In some embodiments, contacting is under conditions sufficient for hybridization of a first primer of the enrichment solid supports to a single-stranded region of a polynucleotide of said single-strand overhang library. In some embodiments, the enrichment solid support comprises a first primer. In some embodiments, the first primer comprises a 3' region identical or homologous to a portion of the non-complementary 5' end of the oligonucleotide. In some embodiments, the method further comprises isolating the enrichment solid supports. In some embodiments, the first primer is a first enrichment primer.

In some embodiments, an enrichment solid support comprises a first enrichment primer. In some embodiments, the solid support is a bead. In some embodiments, the solid support is an artificial solid support. In some embodiments, the first enrichment primer is complementary to the overhang of the polynucleotide. In some embodiments, the first enrichment primer is complementary to the overhang of the oligonucleotide. In some embodiments, the first enrichment primer is identical to the overhang of the first strand. In some embodiments, the first enrichment primer is homologous to the overhang of the first strand. In some embodiments, the first enrichment primer is complementary to the reverse complement of the overhang of the first strand.

In some embodiments, the method further comprises sealing a nick between the first primer and a strand of the polynucleotide of the single-strand overhang library. Thought a single-stranded region of the polynucleotide of the library will hybridize to the first primer the first primer can be ligated to the opposite strand to create a complete strand that now includes the primer. This ligation step will covalently link the strand to solid support. Now if the strand that hybridizes to the first primer should dissociate the oppositive strand will stay attached to the solid support via its integration of the first primer.

Figure 8A:
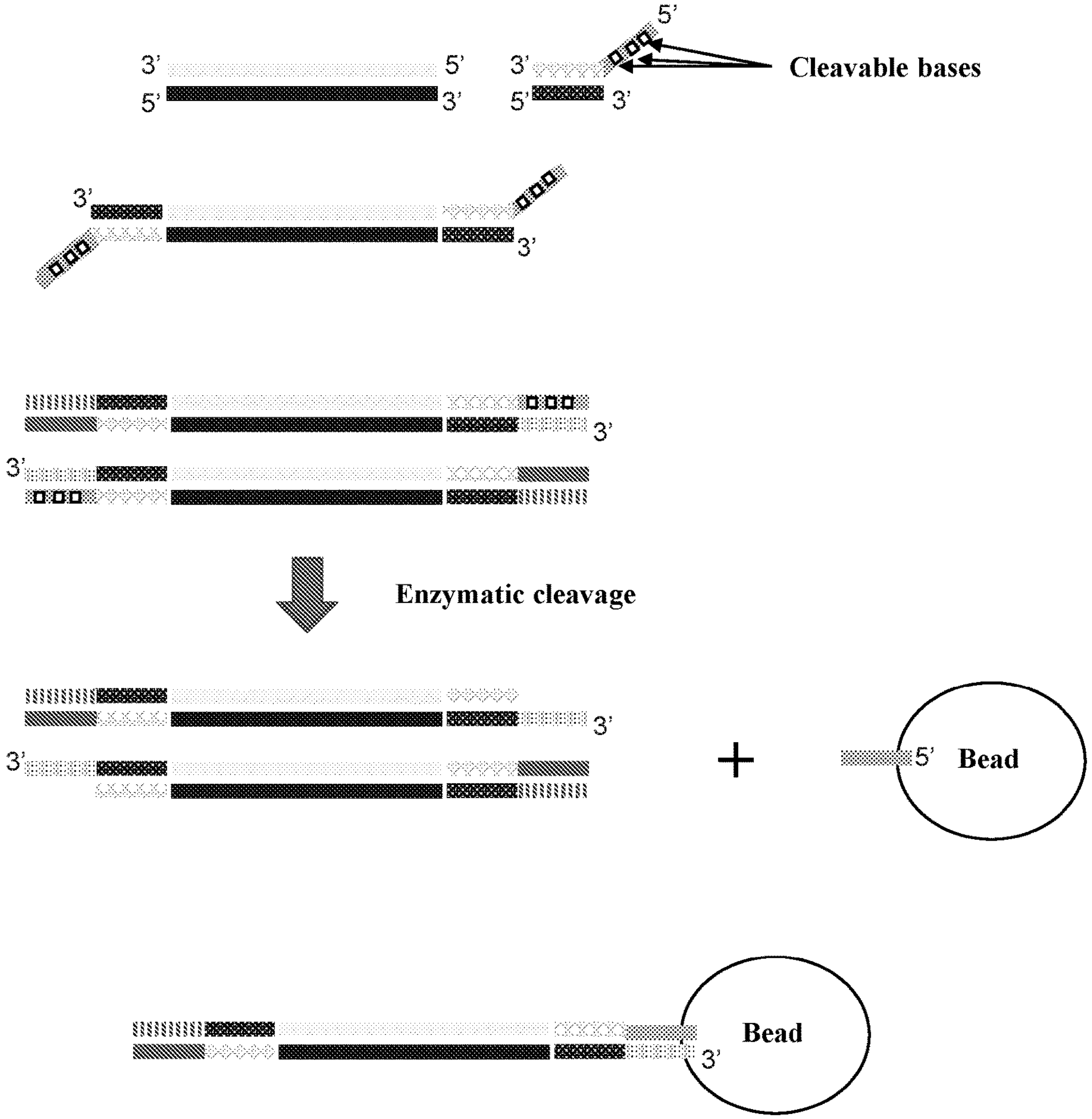
FIGS. 8A-8E are step-by-step diagrams of embodiments of methods of the invention using adapters with cleavable bases for pre-enrichment of template molecules on to beads.
Figure 8A:
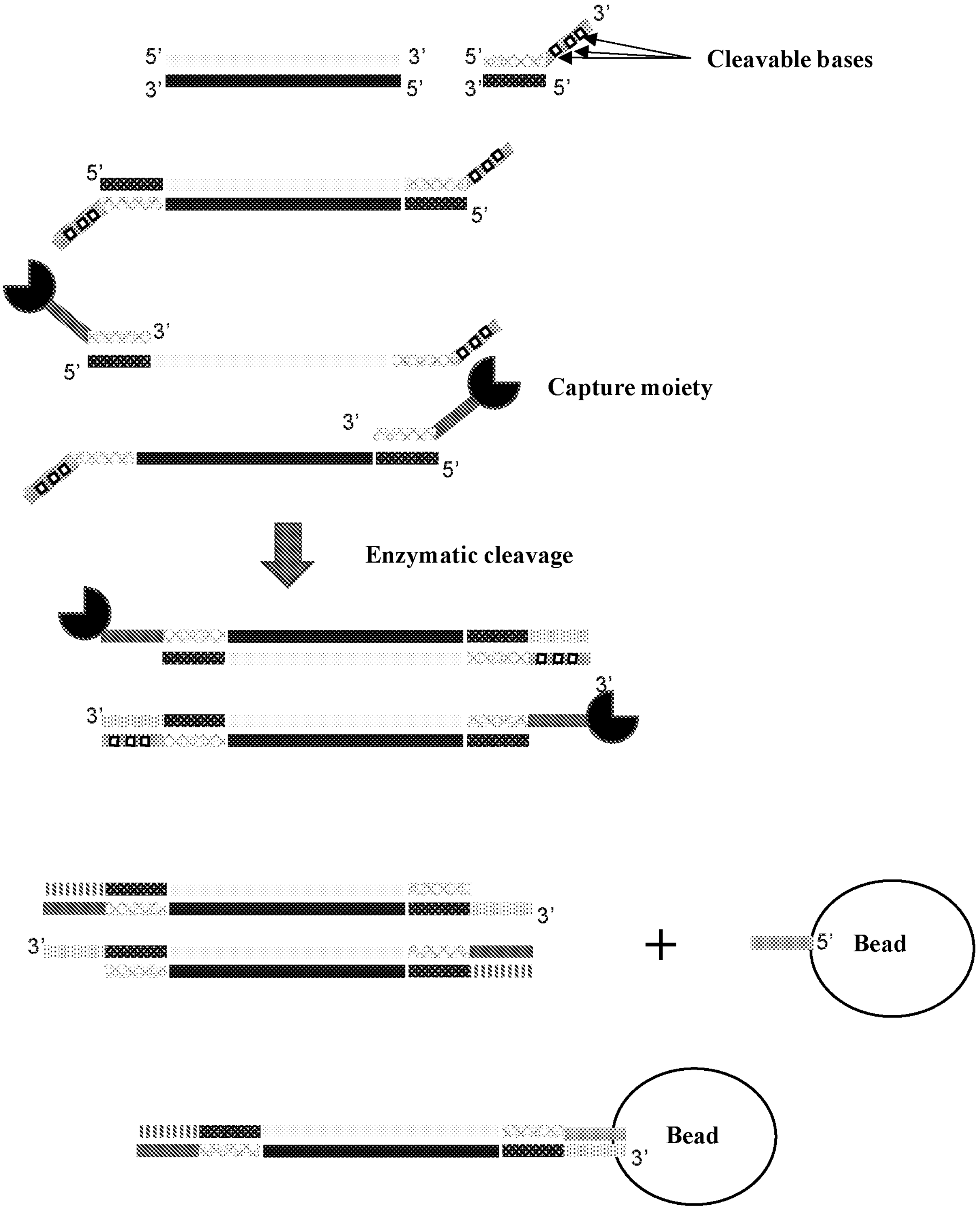

Enrichment can be enhanced by the inclusion of a cleavable or excisable base in the overhang of the first strand. FIG. 8A shows such an embodiment of pre-enrichment. Identical adapters are ligated at both ends of template as described hereinabove, however, the overhang comprises cleavable or excisable bases. Double stranded molecules are generated that comprise different sequences at the 5' and 3' ends by any of the methods described hereinabove. These are the molecules of a sequencing library. At this stage pre-enrichment to a bead can be carried out. One strand of each double stranded molecule will comprise a 5' end region comprising the plurality of cleavable or excisable bases. Excision of the bases by an appropriate enzyme results in dissociation of the overhang region of the first strand of the adapter, leaving a single stranded region at the 3' end of each duplex molecule. Enrichment beads are then added comprising a first primer that is complementary to the single stranded region, and the duplex molecule hybridizes to the enrichment bead. If the bead comprises a single first primer, or very few first primers, only one template molecule from the library will hybridize. A ligation reaction, or nick sealing/filling reaction can be carried out such that one of the strands of the duplex is linked to the bead by the first primer which is now part of that strand.

In some embodiments, the method further comprises adding a solid support to the library. In some embodiments, the solid support is a plurality of solid supports. In some embodiments, the solids support is a bead. In some embodiments, the solid support is an enrichments solid support. In some embodiments, the solid support is a surface. In some embodiments, the solid support is a column. In some embodiments, the solid support is an enrichment support. In some embodiments, the bead is an enrichment bead. In some embodiments, the bead is a sequencing bead. In some embodiments, the bead is an amplification bead. In some embodiments, amplification occurs on the bead. In some embodiments, surface-based amplification occurs on the bead with the attached molecule as template. In some embodiments, the unattached duplex strand is dissociated, and the attached molecule is used as template.

In some embodiments, the method further comprises subjecting the library to conditions sufficient to cleave or excise the cleavable or excisable bases. In some embodiments, the method further comprises subjecting the adapter-target construct and extension product duplex to conditions sufficient to cleave or excise the cleavable or excisable bases. In some embodiments, the cleavage or excision results in dissociation of the overhang region of the first strand from the library molecules. In some embodiments, the cleavage or excision results in dissociation of the overhang region of the first strand from the duplex molecules. In some embodiments, the cleavage or excision results in a single-strand overhang library.

In some embodiments, the method further comprises introducing a solid support to the single-strand overhang library. In some embodiments, the solid support comprises a first primer complementary to the single stranded regions of the single-strand overhang library. In some embodiments, the first primer is identical or homologous to the overhang region of the first strand. In some embodiments, the solid support comprises a plurality of first primers. In some embodiments, the solid support comprises at most 1, 2, 3, 4, or 5 first primers. In some embodiments, the solid support comprises a plurality of second primers. In some embodiments, the second primers are identical or homologous to a 5' region of the first primer. In some embodiments, the second primers are not complementary to any region or sequence in the library. In some embodiments, the second primers are not complementary to any region or sequence in the single-strand overhang library. It will be understood by a skilled artisan that after amplification from the temple strand attached to the bead, the reverse complement of the most 5' region of the first primer will be generated. This complementary strand will be able to bind to the plurality of second primers and clonal amplification on the bead will proceed.

In some embodiments, the adding the solid support is in conditions sufficient for hybridization of a molecule of the single-strand overhang library to the first primer. In some embodiments, the adding results in a single duplex hybridized to a single solid support. In some embodiments, the method further comprises ligating the first primer to a strand of the duplex. In some embodiments, ligating comprises nick filling. In some embodiments, ligating comprises nick sealing. In some embodiments, ligating does not comprise nick filling. In some embodiments, ligating does not comprise nick sealing. In some embodiments, the method further comprises dissociating the strands of the duplex attached to the solid support. In some embodiments, dissociating results in a single template strand attached to the solid support. In some embodiments, the template attached to the solid support is a pre-enrichment product. In some embodiments, the method further comprises isolating the solid support. In some embodiments, the method further comprises isolating the solid support comprising a template molecule. In some embodiments, the method further comprises isolating solid support comprises a duplex molecule. In some embodiments, the isolating does not comprise isolating solid support linked to only adapter sequence. In some embodiments, the isolating does not comprise isolating solids supports devoid of a template molecule.

In some embodiments, the isolating comprises isolating enrichment solid supports comprising polynucleotide of the single-strand overhang library. In some embodiments, the isolating comprises isolating enrichment solid supports comprising single polynucleotide of the single-strand overhang library. In some embodiments, the isolating comprises isolating enrichment solid supports comprising a clonal population of a single polynucleotide of the single-strand overhang library. In some embodiments, isolating comprises isolating function enrichment solid supports. In some embodiments, functional enrichment solid supports are solid supports capable of being used in a downstream enzymatic reaction. In some embodiments, the enzymatic reaction is amplification. In some embodiments, the enzymatic reaction is sequencing.

In some embodiments, attached comprises covalently linked. In some embodiments, the first primer is covalently linked to the solid support. In some embodiments, the pre-enrichment product is a template nucleic acid linked to a solid support. In some embodiments, the method further comprises amplifying the library. In some embodiments, the method further comprises amplifying the template of the pre-enrichment product. In some embodiments, the amplifying comprises adding a polymerase. In some embodiments, the amplifying comprises adding reagents sufficient for amplification. In some embodiments, the amplification comprises adding a soluble primer. In some embodiments, the soluble primer hybridizes to the 3' end of the template strand. In some embodiments, the soluble primer is a sequencing primer.

Figure 8B:
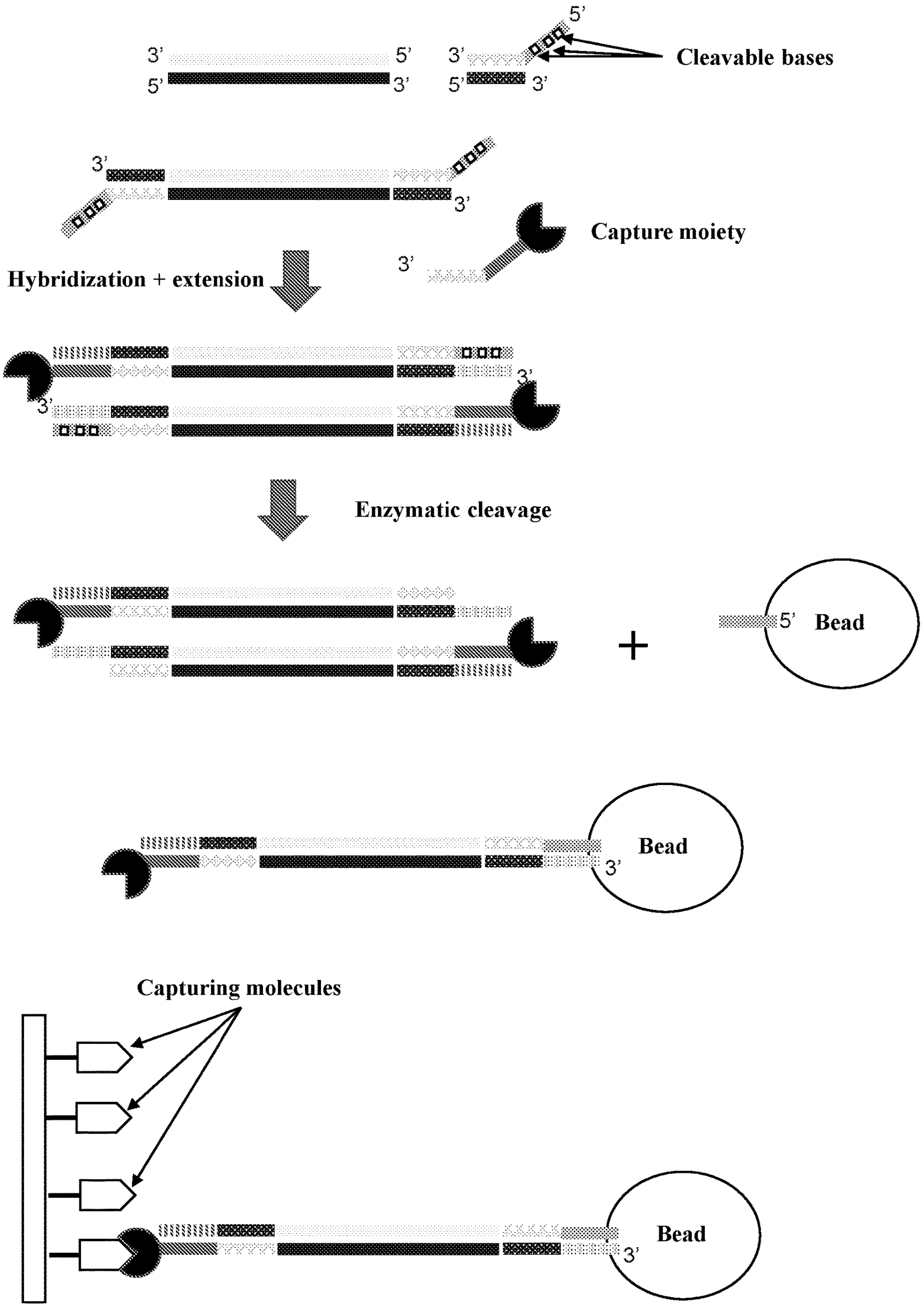

In some embodiments, the oligonucleotide comprises a capture moiety. In some embodiments, the capture moiety is at the 5' end of the oligonucleotide. In some embodiments, the solid support does not bind the capture moiety. As can be seen in FIG. 8B, when the duplex is attached to the solid support the, the strand comprising the capture moiety is not the strand linked to the solid support but rather is the complementary strand. Thus, the enrichment beads can be put in contact with the capturing molecule and only beads that have a fully library product attached will be captured by the capturing molecule. The rest of beads, whether empty, or comprising only adapter or adapter dimers will not bind the capturing molecule. The result is that only functional enrichment beads are retained. The capturing molecule can be on a column for example, such as is depicted in FIG. 8B and non-enriched beads will pass through the column and not be retained. In order to release the enrichment beads from the capturing molecule, simple dissociation of the duplex is all that is required. This results in a single strand attached to the now recovered enrichment beads.

In some embodiments, the method further comprises contacting the library with a capturing molecule. In some embodiments, the method further comprises contacting the capturing molecule under conditions sufficient for binding of the capturing molecule to the capture moiety. In some embodiments, the capturing molecule is contacted to the enrichment beads. In some embodiments, the capturing molecule is contacted to the enrichment beads comprising bound duplex. In some embodiments, the capturing molecule is attached to a solid support. In some embodiments, the capturing molecule is on a bead. In some embodiments, the capturing molecule is on a column. In some embodiments, the capturing molecule is contacted to the pre-enrichment solution. In some embodiments, the capturing molecule is contacted to the library solution. In some embodiments, the capture with the capturing molecule removes non-enriched solid supports. In some embodiments, a non-enriched solid support is a solid support devoid of a template molecule. In some embodiments, a non-enriched solid support is a soldi support linked to only adapter. In some embodiments, a non-enriched solid support is a solid support comprising a template molecule with identical adapters at each end. In some embodiments, an enriched solid support comprises a template molecule with a different adapter at each end. In some embodiments, the method further comprises isolating the capturing molecule.

Figure 8C:
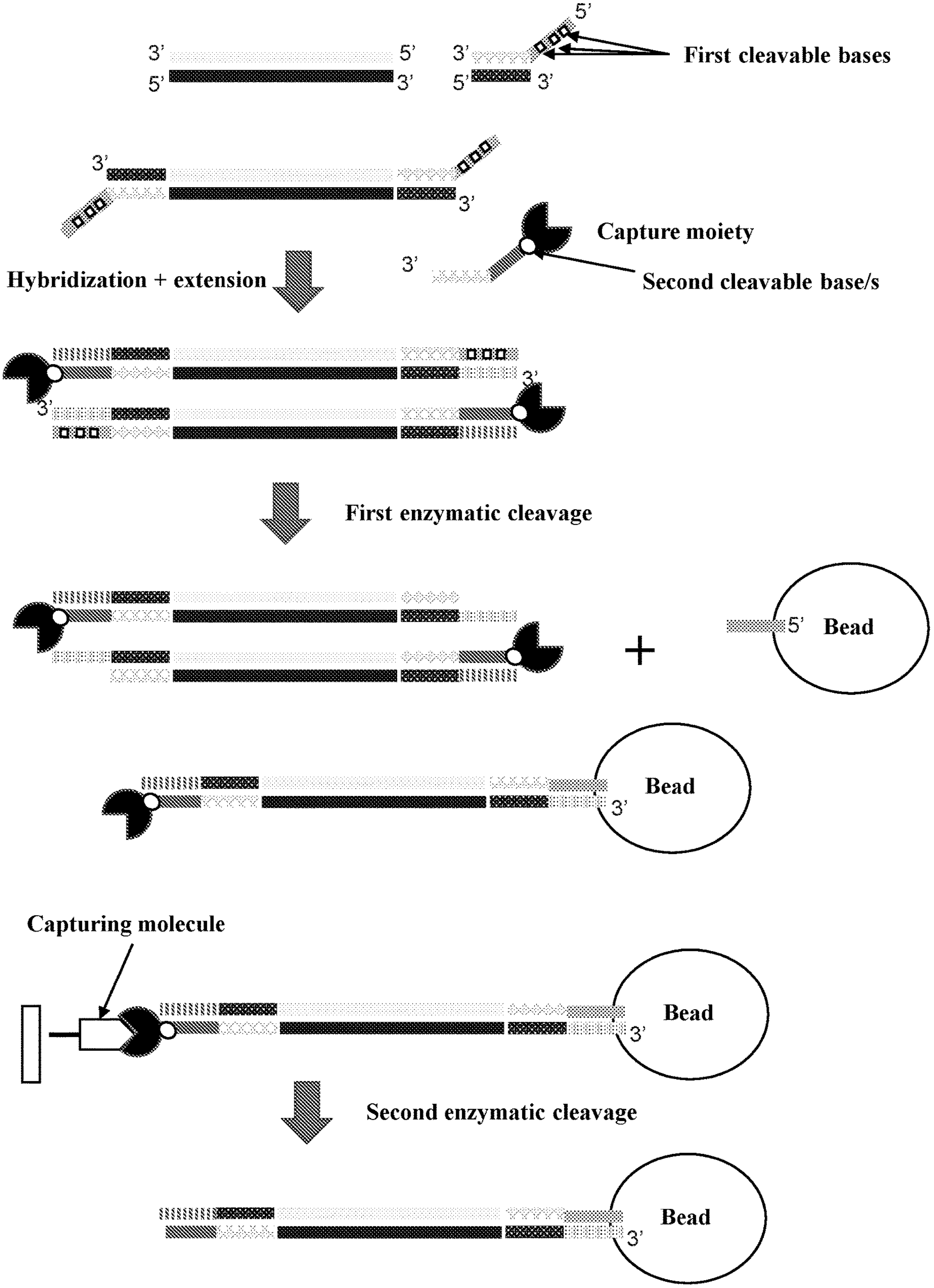

In embodiments, in which it is desired to have a duplex product adhered to the enrichment beads the oligonucleotide can comprise a cleavable or excisable base proximal to the capture moiety (see for example FIG. 8C). This proximal cleavage or excisable base within the oligonucleotide would be a different moiety than is in the first strand of the adapter. For example, the first cleavable or excisable base could be a uracil and cleavage would proceed with the USER™ enzyme (a mixture of UDG and endonuclease VIII) and the second cleavable or excisable base could be a non-uracil RNA base and cleavage is with an RNaseH. After capture to the capturing molecule, the enzymatic digestion removes the capture moiety from the duplex and the enriched bead is released with a bound duplex.

Figure 8D:
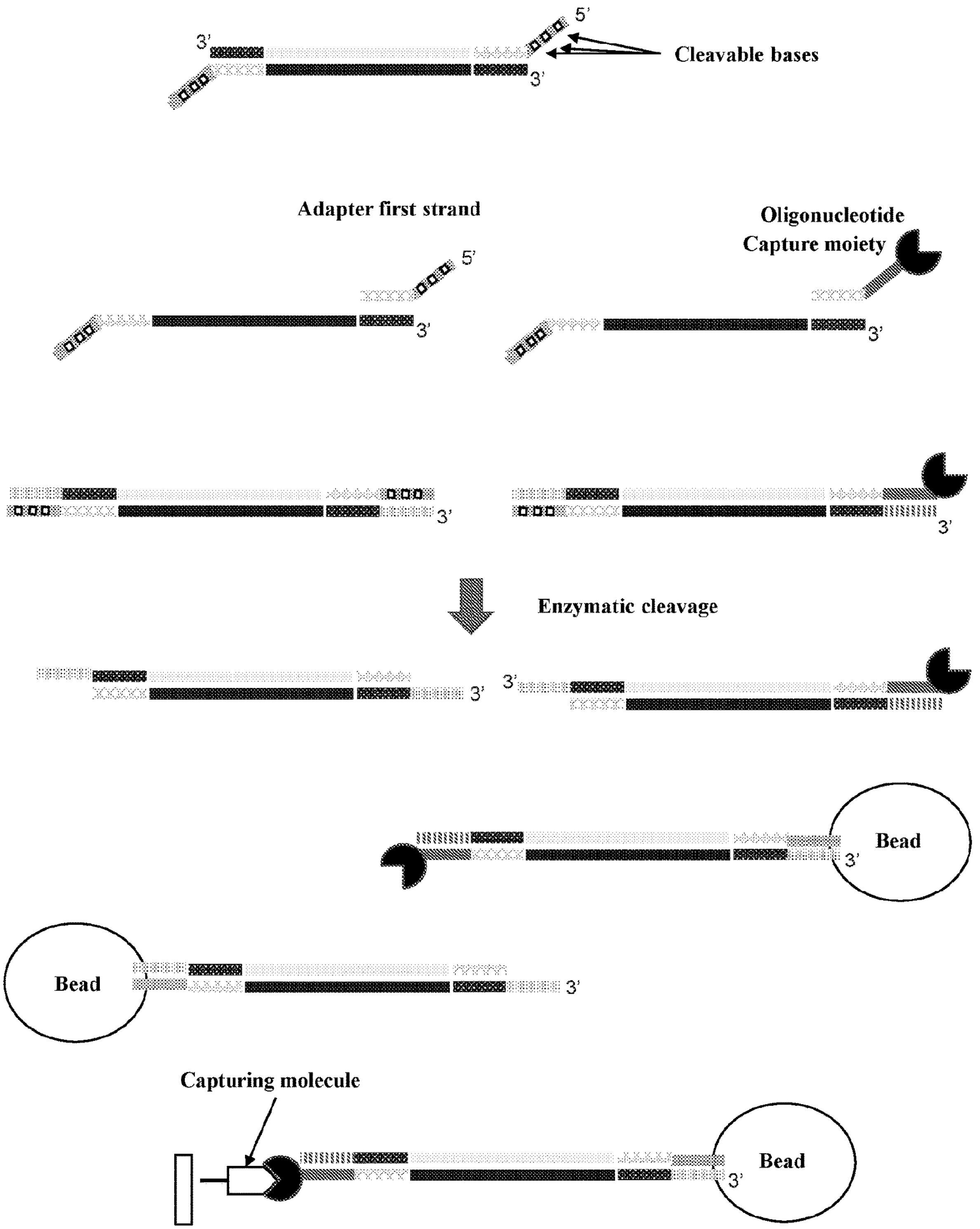

Use of a capturing molecule also eliminates contamination by molecules produced by extension from a dissociated adapter and not from the oligonucleotide. If the adapter is not removed or is only partially removed, upon dissociation of the template molecule, the adapter will also dissociate. The single strands of the adapter will then compete with the oligonucleotide to primer the extension reaction. As only the oligonucleotide comprises the capture molecule, any extension from the adapter strands will result in duplex that, while capable of binding to the enrichment solid support cannot be captured by the capturing molecule. These defective duplex molecules will have the same adapter at both ends of the template and while then will be present on the enrichment beads, use of the capturing molecule removes then from the library and thus improves downstream reaction (i.e. sequencing). One such embodiment is presented in FIG. 8D.

Figure 8E:
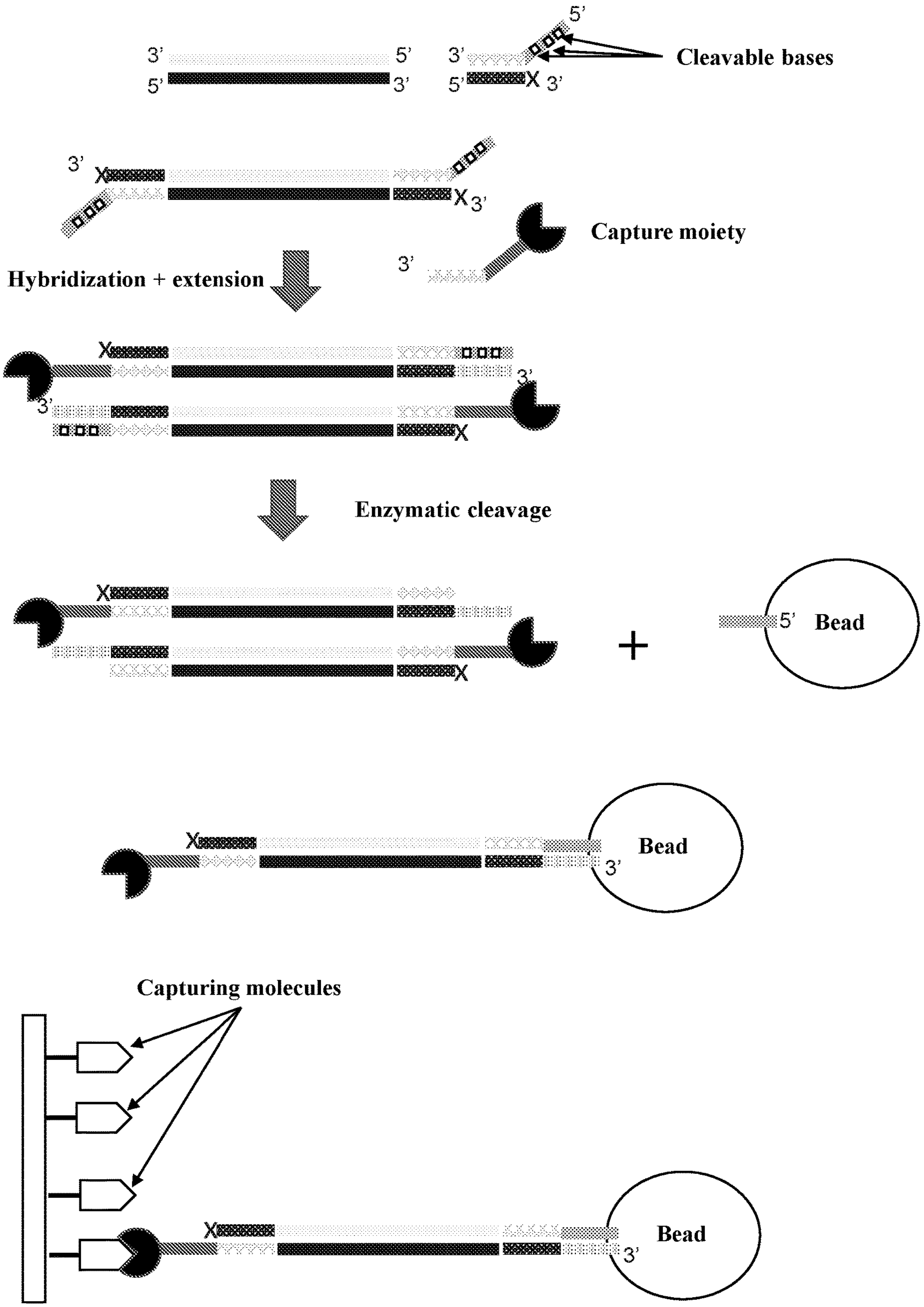

It will be evident to a skilled artisan that the embodiments presented in FIG. 8A-8D are compatible with an adapter molecule that is 3' blocked on the second strand, such as is shown in FIG. 5. Such an embodiment is presented in FIG. 8E. In such an embodiment, the soluble primer added during amplification would hybridize to the 3' end of the template strand attached to the solid support. In some embodiments, the soluble primer is identical or homologous to the oligonucleotide.

Alternatively, the 3' end of the duplex that is complementary to the first primer on the solid support, when introduced to a polymerase would act as a primer and would synthesize a reverse complement to the entirety of the first primer on the solid support. In embodiments, in which the 5' end of the first primer is identical or homologous to the plurality of second primers on the solid support, the newly synthesized reverse complementary region could "walk" to the next primer and elongation would initiate from this second primer. In this way amplification can proceed without the addition of a soluble primer. Such template walking can occur when the template molecule is a duplex, and the presence of a blocked adapter is irrelevant. When the template is single stranded, a primer complementary to the 3' end of the single strand must be present. This primer may be the soluble primer. Alternatively, the solid support may comprise a third population of primers that are reverse complements to the 3' end of the template. This will result in a bridge amplification occurring on the surface of the bead. In some embodiments, the enrichment bead comprises a first primer, a population of second primer and a population of third primers. Methods of amplification from beads are further described in International Patent Publication WO2020/167656 herein incorporated by reference in its entirety.

In some embodiments, the oligonucleotide comprises a capture moiety 5' to at least one cleavable or excisable base. In some embodiments, the cleavable or excisable base in the oligonucleotide is cleaved or excised by different conditions than the cleavable or excisable bases in the overhang of the first strand. In some embodiments, excision of the cleavable bases from the oligonucleotide induces removal of the capture moiety from the polynucleotide of the library.

In some embodiments, isolating comprises contacting the single-strand overhang library and enrichment solid supports with the capturing molecule. In some embodiments, the contacting is under conditions sufficient for binding of the capturing molecule to the capture moiety. In some embodiments, the isolating further comprises isolating the capturing molecule. In some embodiments, the isolating further comprises subjecting the isolated capturing molecule to conditions sufficient to cleave or excise the cleavable or excisable bases of the oligonucleotide. In some embodiments, the subjecting dissociates the enrichment solid supports linked to a library polynucleotide from the capturing molecule. In some embodiments, the subjecting produces isolated enriched solid supports. In some embodiments, the subjecting produces isolated enrichment solid supports enriched with a library polynucleotide. In some embodiments, the enrichment is enriched by a clonal population of a library polynucleotide.

In some embodiments, the polynucleotide of the library is pre-bound to an enrichment solids support. In some embodiments, the capturing molecule is used to isolate pre-enriched solid supports. In some embodiments, the capturing molecule is used to isolate enrichment beads with a library polynucleotide attached.

In some embodiments, the method further comprises performing amplification on the pre-enriched solid support. In some embodiments, the method further comprises performing amplification on the solid support comprising the template molecule. In some embodiments, amplification is clonal amplification. Any method of amplification known in the art may be employed, such as for non-limiting example surface PCR, emPCR, and recombinase polymerase amplification (RPA). In some embodiments, the amplification is isothermal amplification. In some embodiments, the amplification is emPCR. In some embodiments, the amplification is RPA. In some embodiments, the amplification is bridge amplification. In some embodiments, the bridge amplification is bridge PCR. In some embodiments, the bridge amplification is bridge emPCR. In some embodiments, the bridge amplification is bridge RPA.

Kit

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

By another aspect, there is provided a kit comprising a polynucleotide of the invention.

In some embodiments, the kit comprises the herein disclosed polynucleotide; and a DNA oligonucleotide comprising a nucleic acid sequence complementary to the annealed portion of the herein disclosed polynucleotide. In some embodiments, the kit further comprises a DNA oligonucleotide comprising a nucleic acid sequence complementary to the annealed portion of the herein disclosed polynucleotide. In some embodiments, the oligonucleotide is an oligonucleotide as described hereinabove. In some embodiments, the oligonucleotide comprises a capture moiety. In some embodiments, the kit comprises a capturing molecule. In some embodiments, the oligonucleotide comprises at least one cleavable or excisable base.

In some embodiments, the kit further comprises: a solitary purine and a solitary pyrimidine, a DNA ligase, an RNA ligase, a DNA polymerase, an RNA polymerase, or any combination thereof.

In one embodiment, the kit as described herein comprise a PCR buffer. In one embodiment, a PCR buffer comprises: 5 to 100 mM Tris-HCl and 20 to 100 mM KCl. In one embodiment, a PCR buffer further comprises 10 to 100 mM Magnesium Chloride. In one embodiment, the kit as described herein comprise a dNTP mixture. In one embodiment, the kit as described herein comprise DNA Polymerase such as but not limited to Taq DNA Polymerase. In one embodiment, the kit as described herein comprises distilled water.

In some embodiments, the kit comprises a cleaving agent. In some embodiments, the cleaving agent is capable of cleaving a cleavable or excisable base in the polynucleotide of the kit. In some embodiments, the cleaving agent is capable of cleaving a cleavable or excisable base in the oligonucleotide of the kit. In some embodiments, the kit comprises a plurality of cleaving agents. In some embodiments, the kit further comprises the oligonucleotide. In some embodiments, the polynucleotide comprises a first cleavable or excisable base and the oligonucleotide comprises a second cleavable or excisable base and the kit comprises a first cleaving agent capable of cleaving the first cleavable or excisable base and a second cleaving agent capable of cleaving the second cleavable or excisable base. In some embodiments, the polynucleotide comprises two different kinds of cleavable or excisable bases and the kit comprises different cleaving agents for each kind of cleavable or excisable base.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a", "an", and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Unless specifically stated or obvious from context, as used herein, the term "or" is understood to be inclusive.

Throughout this specification and claims, the word "comprise," or variations such as "comprises" or "comprising," indicate the inclusion of any recited integer or group of integers but not the exclusion of any other integer or group of integers.

As used herein, the term "consists essentially of" or variations such as "consist essentially of" or "consisting essentially of" as used throughout the specification and claims, indicate the inclusion of any recited integer or group of integers, and the optional inclusion of any recited integer or group of integers that do not materially change the basic or novel properties of the specified method, structure or composition.

As used herein, the terms "comprises", "comprising", "containing", "having" and the like can mean "includes", "including", and the like; "consisting essentially of or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments. In one embodiment, the terms "comprises," "comprising, "having" are/is interchangeable with "consisting".

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Example 1

The following describes the exposition of one embodiment of the invention as described above. Purified human DNA is supplied, either from a cell line or a primary sample. The DNA is fragmented in preparation for the ligation of the adapters of the invention. The double stranded DNA (dsDNA) may be end repaired to ensure blunt ends and phosphorylation. Blunt end ligation is performed with the prepared dsDNA and the adapters of the invention. The product of the reaction is isolated, and unbound adapter is removed. Optionally, unreacted dsDNA fragments may also be removed.

The double-stranded ligation product is denatured, and either a PCR-free protocol (e.g., a single extension step), a limited PCR protocol (e.g., 3-6 cycles) or a full PCR protocol (e.g., 35-40 cycles) is performed using a first primer or second adapter to produce dsDNA with different adapters at the 5' and 3' ends. In some embodiments, a PCR-free, single extension is performed. In some embodiments, a PCR reaction is performed. In some embodiments, the PCR reaction is a limited PCR reaction. In some embodiments, the PCR reaction is a full PCR reaction. In some embodiments, a full PCR reaction comprises at least 20, 25, 30, 35, 36, 37, 38, 39 or 40 cycles. Each possibility represents a separate embodiment of the invention. This library is then used for clonal expansion, and sequencing.

Example 2

Solid supports comprising a template nucleic acid molecule coupled thereto, as described herein, were prepared. In a first experiment biotin labeled nucleic acids were used and in a second experiment the biotin labeled nucleic acids also contained cleavable bases to facilitate release from the magnetic beads used for collection. The following procedures were used.

Annealing and extension of library strands to generate a bead-attached template: A reaction mixture containing a final volume of 100 microliters was prepared with the following components/concentrations: 1 10×TAQ polymerase reaction buffer, 8.2 millimolar (mM) of MgCb, 12 mM of dNTP, 10 picomolar (pM) of the library (from artificial templates), 1 micromol/min (U) Taq DNA polymerase, and $6.00\times10^7$ beads/microliter. The library contained molecules which were biotinylated due to the use of a biotinylated oligonucleotide during extension. The molecules did not contain cleavable bases. The mixture was incubated in a thermocycler using the conditions: 95 degrees Celsius for 5 minutes, 50 degrees Celsius for 1 hour, 70 degrees Celsius for 1 hour and a short 12 degree Celsius soak.

The beads were washed by adding 400 microliters (μL) of TET Buffer (TE pH 8.0, 0.05% Triton X-100). The mixture was vortexed for 30 seconds and spun down at 21,000 revolutions per minute (RPM) for 8 minutes in a centrifuge. The supernatant was removed to leave 100 μL. The beads were washed with 500 μL of lx SA Bind Buffer (20 mM Tris pH 3.0, 50 mM NaCl, 0.05% Triton X-100). The mixture was vortexed for 30 seconds and spun down at 21,000 RPM for 8 minutes in a centrifuge. The supernatant was removed to leave 100 μL.

Enriching the extended beads: 100 μL of magnetic Streptavidin beads (NEB) were added to the pre-enriched beads. This mixture was mixed and incubated for 1 hour at room temperature. The beads were magnetized on an appropriate magnet until the solution was clear, and the supernatant was removed. The beads were washed twice with 500 μL of SA Bind Buffer (20 mM Tris pH 3.0, 50 mM NaCl, 0.05% Triton X-100) by gentle resuspension. Each wash was followed by a magnetization operation, in which the beads were magnetized on an appropriate magnet until the solution was clear, and the supernatant was removed.

Figure 9A:
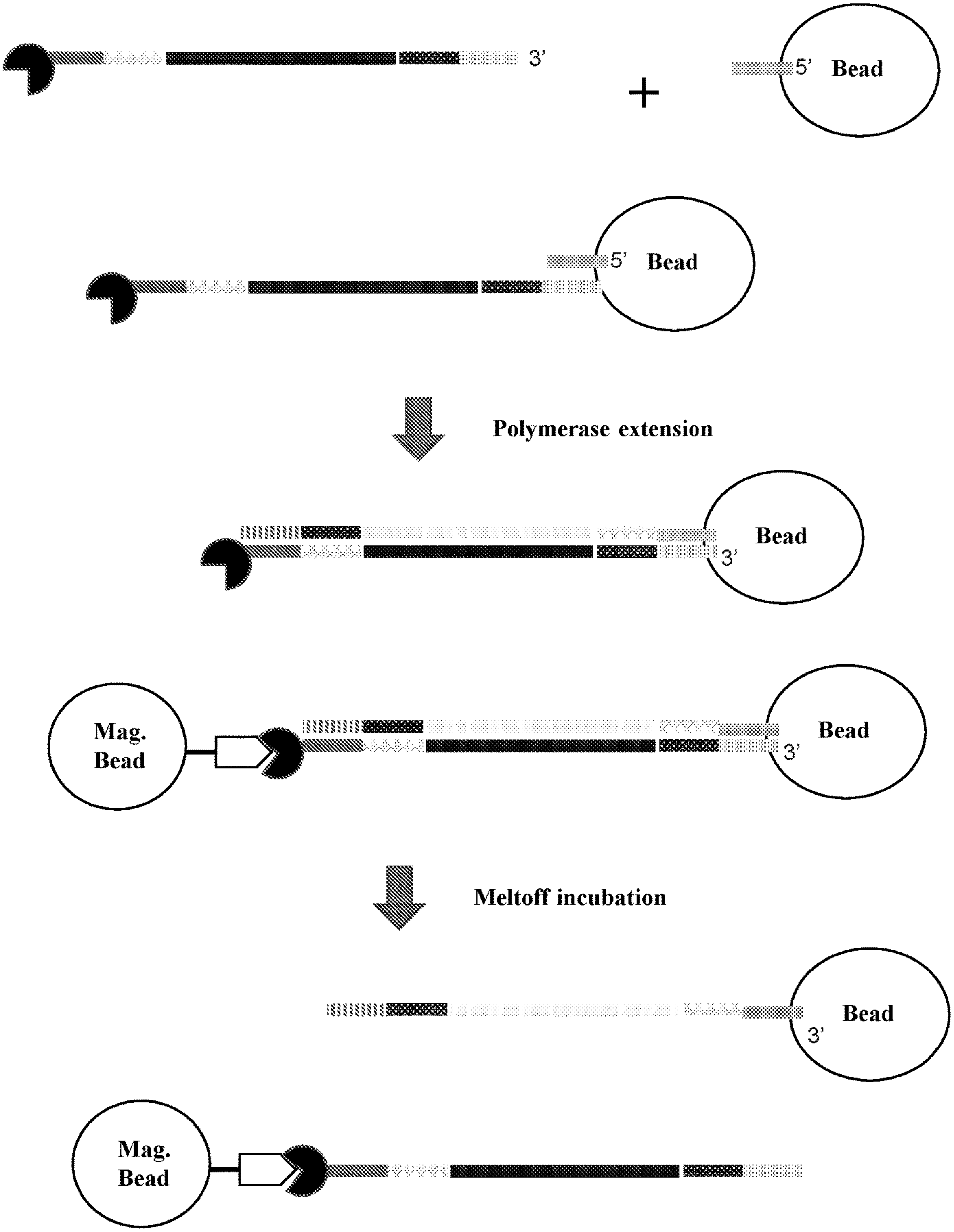
FIG. 9A-9C are step-by-step diagrams of embodiments of methods of preindictment (9A) without cleavable bases, (9B) with a single type of cleavable base, and (9C) with two different types of cleavable bases.

Eluting the enriched beads by strand disruption: The mix of amplification and magnetic beads was resuspended in 300 μL of 50° C. Meltoff Buffer (0.1 mol/liter (M) NaOH, 0.05% Triton X-100), and incubated for 5 minutes at 50° C. The mixture was vortexed briefly and the beads were magnetized on an appropriate magnet until the solution was clear. The supernatant containing the amplification beads and single stranded template were removed and retained. In a second melt-off operation, the beads were resuspended in 300 μL of 50° C. Meltoff Buffer (0.1 mol/liter (M) NaOH, 0.05% Triton X-100), and incubated for 5 minutes at 50° C. The mixture was vortexed briefly and the beads were magnetized on an appropriate magnet until the solution was clear. The supernatant containing the amplification beads and single stranded template were removed and retained and combined with the earlier supernatant containing the beads. This protocol is summarized schematically in FIG. 9A.

Figure 9B:
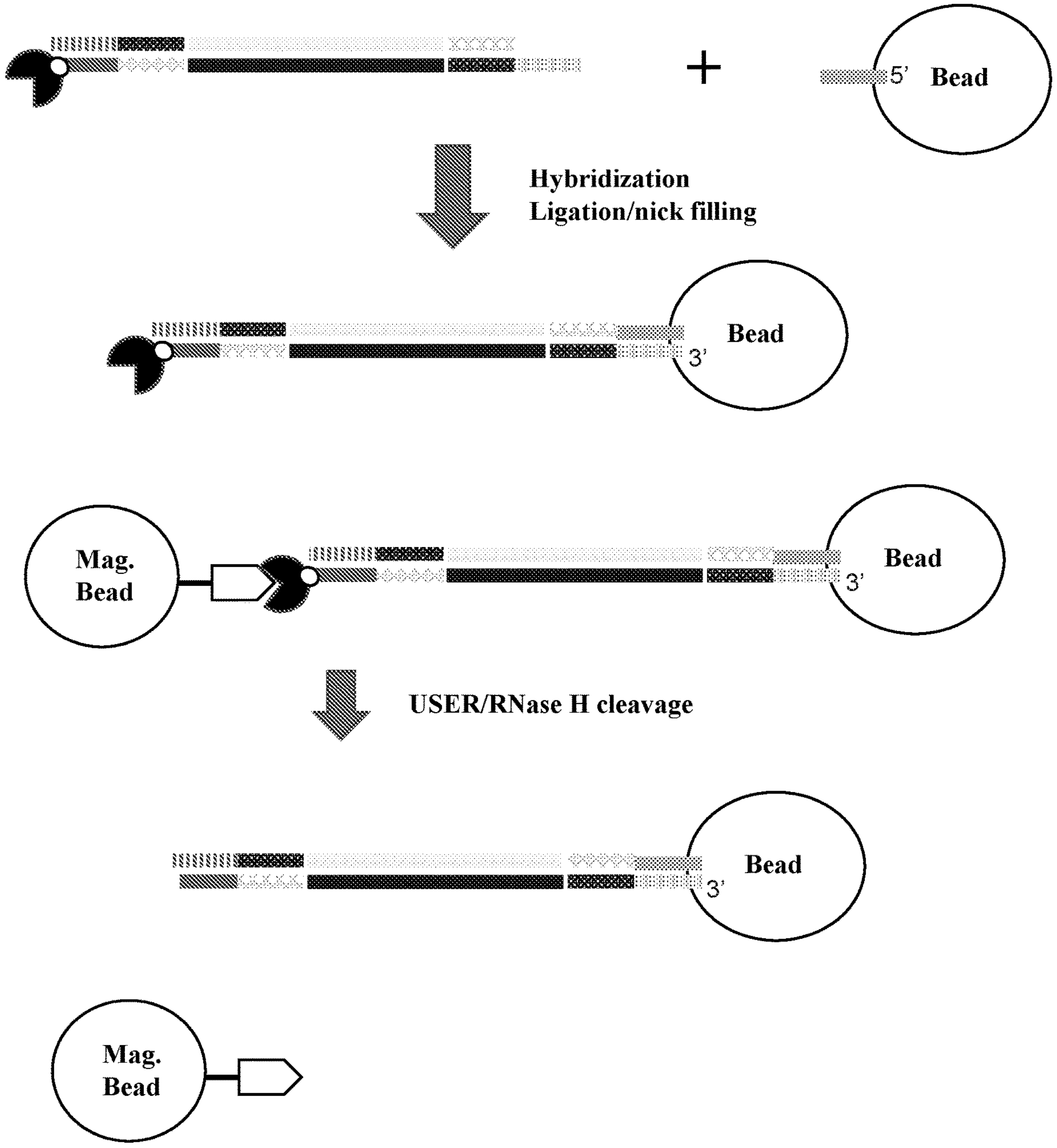

In parallel the following protocol was performed, which is summarized schematically in FIG. 9B.

Annealing and ligating library duplex to amplification beads to generate a bead-attached template: A reaction mixture containing a final volume of 250 microliters was prepared with the following components/concentrations: 1 10×TAQ ligase reaction buffer, 5 picomolar (pM) of the library (from artificial templates), 0.8 micromol/min (U) Taq DNA polymerase, and $6.00\times10^7$ beads/microliter. The library contained molecules which were biotinylated due to the use of a biotinylated oligonucleotides/primers during library generation. The primers also contained three cleavable bases just 3' to the 5' biotinylated base. Two such libraries were generated, one with uracil DNA bases and one with ribonucleic acid bases (uracils). The mixture was incubated at 45 degrees Celsius for 1 hour. The following was performed for each library separately.

Enriching the beads with template: The 250 μL of ligation reaction was diluted in 750 μL of TET Buffer (TE pH 8.0, 0.05% Triton X-100) and mixed with 250 μL of streptavidin beads. This mixture was mixed and incubated for 2 hours at room temperature. The beads were magnetized on an appropriate magnet until the solution was clear, and the supernatant was removed. The beads were washed twice with 500 μL of SA Bind Buffer by gentle resuspension. Each wash was followed by a magnetization operation, in which the beads were magnetized on an appropriate magnet until the solution was clear, and the supernatant was removed.

Eluting the enriched beads by enzymatic cleavage: The mix of amplification product containing uracils and magnetic beads was resuspended in 100 μL of TET Buffer with 3 μL (1 unit/μL) of USER™ enzyme (NEB) (a mixture of UDG and endonuclease VIII) and was incubated at 37 degrees Celsius for 30 minutes. The mix of amplification product containing RNA bases and magnetic beads was resuspended in 100 μL of TET Buffer with 2 μL of RNase HII (5 units/μL) and was incubated at 37 degrees Celsius for 30 minutes. The mixture was vortexed briefly and the beads were magnetized on an appropriate magnet until the solution was clear. The supernatant containing the amplification beads and duplex template were removed and retained.

Both sets of eluted beads were spun down at 21,000 RPM for 8 minutes in a centrifuge, and the supernatant was removed to leave 100 μL. The beads were washed with 500 μL of lx SA Bind Buffer, and vortexed for 30 seconds. The beads were spun down at 21,000 RPM for 8 minutes in a centrifuge, and the supernatant was removed to leave 100 μL. The beads were washed with 500 μL of TET Buffer, and vortexed for 30 seconds. The beads were spun down at 21,000 RPM for 8 minutes in a centrifuge, and the supernatant was removed to leave 100 μL.

Flow cytometry was used to count the input beads and the beads recovered after pre-enrichment. Pre-enrichment using strand dissociation and not enzymatic cleavage resulted in 1.6% enrichment (against a theoretical 10%). In contrast, the cleavage protocol using USER™ (a mixture of UDG and endonuclease VIII) cleavage of uracils resulted in about the target 10% enrichment, while the RNase H treatment produced a 5% enrichment. Thus, both cleavable moiety methods were significantly superior to the dissociation method, though the USER™ enzyme (a mixture of UDG and endonuclease VIII) was twice as effective as RNase.

The enriched beads were subsequently used in emPCR procedures, and the libraries pre-enriched on beads were found to be functional.

Example 3

Figure 9C:
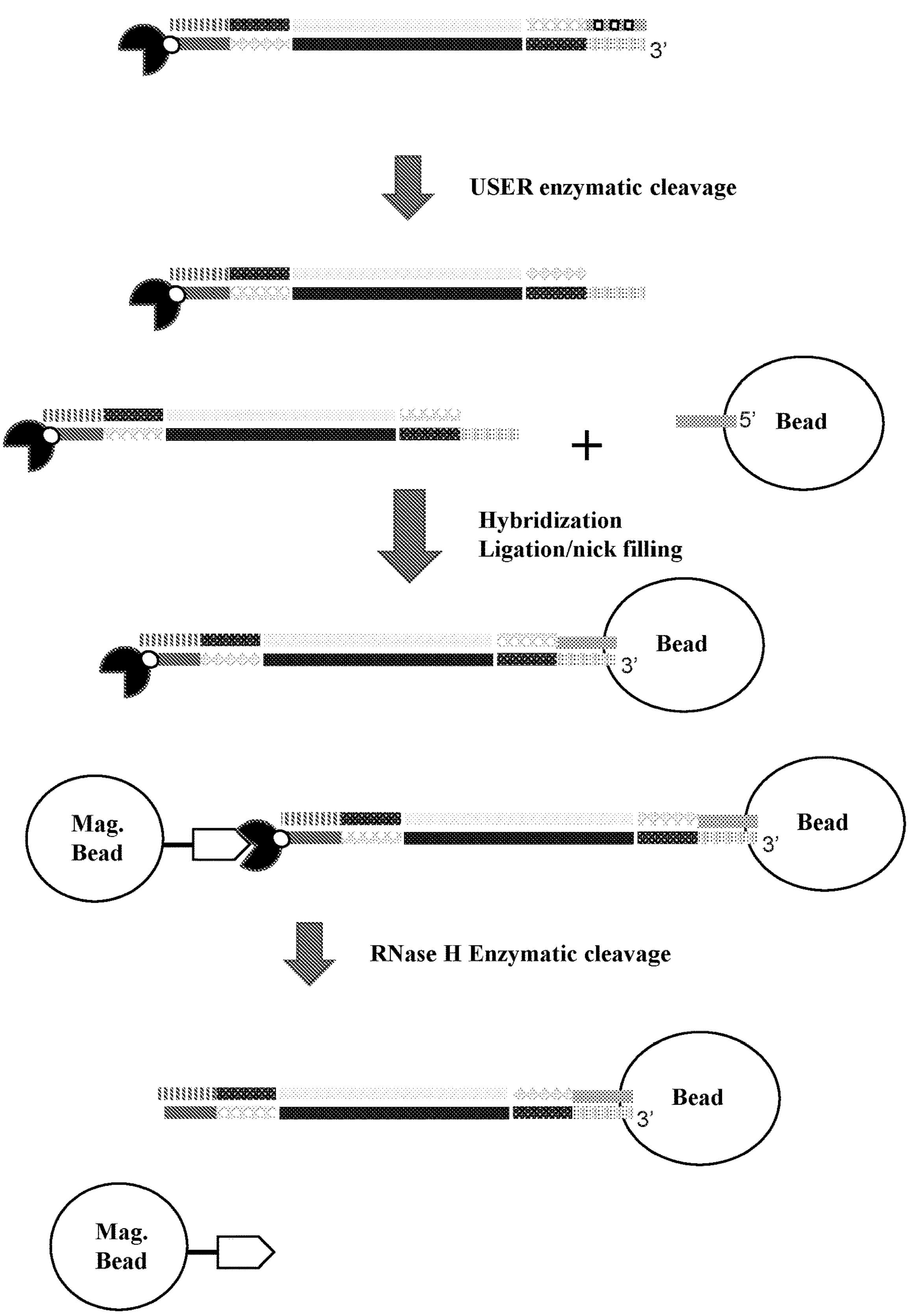

Based on the success of the pre-enrichment protocols using USER™ (a mixture of UDG and endonuclease VIII) and RNaseH, a double digestion pre-enrichment (see FIG. 8C) was tested. This protocol is summarized schematically in FIG. 9C.

The library was generated using adapters that contained four uracil DNA bases in the first strand overhang (GGTCGCUGTCACCUGCTGCUGATTTCU, SEQ ID NO: 1). The oligonucleotide/primer as before was biotinylated with three RNA bases (uracils) downstream of the biotinylated base (Biotin-UCCAUCT-CAUCCCTGCGTGTCTCCGA, SEQ ID NO: 2). The library duplex molecules were incubated with 3 μL of USER™ enzyme (a mixture of UDG and endonuclease VIII) at 37 degrees Celsius for 30 minutes to generate a single-stranded region. Annealing and ligation to the amplification beads was carried out as before using TAQ ligase. The beads bound to template were mixed and incubated with magnetic streptavidin beads, cleaved with RNase HII and free beads and duplex template were isolated as before.

Flow cytometry was again used to count the input and recovered beads. The double cleavage method resulted in ~30% enrichment (against a theoretical ~66%). This method was not as efficient as the USER™ (a mixture of UDG and endonuclease VIII) alone pre-enrichment method but was still significantly superior to the pre-enrichment without any cleavage to release the beads/template.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

What is claimed is:

1. A method for generating a library of different polynucleotide molecules, the method comprising:

(a) providing a plurality of different target double-stranded polynucleotides;

(b) providing polynucleotide adapters, wherein each polynucleotide adapter comprises:

(i) a double-stranded annealed region comprising a first strand and a second strand annealed to each other at a first strand region of complementarity and a second strand region of complementarity, respectively, wherein said second strand comprises a plurality of cleavable or excisable bases in said second strand region of complementarity; and (ii) a 5' overhang region on said first strand;

(c) ligating said polynucleotide adapters to both ends of said different target double-stranded polynucleotides to form adapter-target constructs;

(d) subjecting said adapter-target constructs to conditions sufficient to cleave or excise respective pluralities of cleavable or excisable bases, thereby dissociating respective second strands from respective first strands of said polynucleotide adapters; and (e) annealing an oligonucleotide to said first strand region of complementarity of said adapter-target constructs; thereby generating a library of different polynucleotide molecules.

2. The method of claim 1, wherein said ligating in (c) comprises ligating a respective 3' end of a respective first strand of said polynucleotide adapters to each end of said different target double-stranded polynucleotides.

3. The method of claim 1, wherein said subjecting in (d) comprises bringing said adapter-target constructs in contact with a cleaving agent that cleaves or excises said respective pluralities of cleavable or excisable bases.

4. The method of claim 3, wherein said cleaving agent is selected from the group consisting of uracil DNA glycosylase (UDG), apyrimidinic/apurinic endonuclease (APE), endonuclease, endonuclease VIII (EndoVIII), endonuclease V (EndoV), a mixture of UDG and endonuclease VIII, formamidopyrimidine DNA glycosylase (Fpg), 8-oxoguanine glycosylase (OGG1), RNase, RNaseH, RNaseHII, and ultraviolet light.

5. The method of claim 1, wherein said oligonucleotide comprises a 3' region that is not complementary to said first strand of said polynucleotide adapters.

6. The method of claim 1, wherein said 5' overhang region on said first strand comprises at least 9 nucleotides.

7. The method of claim 1, wherein said different target double-stranded polynucleotides are selected from the group consisting of genomic DNA or fragments thereof, cell-free DNA, and complementary DNA (cDNA).

8. The method of claim 1, wherein said different target double-stranded polynucleotides are a plurality of target DNA molecules comprising different sequences.

9. The method of claim 1, wherein said library of different polynucleotide molecules comprises different double-stranded polynucleotide molecules each comprising regions of non-complementarity at a 5' end and a 3' end.

10. The method of claim 1, wherein, in said ligating in (c), said polynucleotide adapters are provided in excess of said different target double-stranded polynucleotides by a molar ratio of more than 200:1.

11. The method of claim 1, wherein said subjecting in (d) further comprises subjecting an adapter dimer generated in said ligating in (c) to said conditions sufficient to cleave or excise said plurality of cleavable or excisable bases, thereby degrading said adapter dimer.

12. The method of claim 1, wherein said oligonucleotide comprises a capture moiety, and said method further comprises contacting said library with a capturing molecule under conditions sufficient to bind said capturing molecule to said capture moiety, and isolating said capturing molecule.

13. The method of claim 2, wherein said oligonucleotide comprises said capture moiety located 5' to at least one cleavable or excisable base, wherein said at least one cleavable or excisable base in said oligonucleotide is cleaved or excised by different conditions than said conditions for cleaving or excising said plurality of cleavable or excisable bases in said second strand, and wherein excision of said at least one cleavable or excisable base from said oligonucleotide induces removal of said capture moiety from a polynucleotide molecule of said library comprising said oligonucleotide; and said method further comprises (i) contacting said library with said capturing molecule under conditions sufficient to bind said capturing molecule to said capture moiety;

(ii) isolating said capturing molecule; and (iii) subjecting said capturing molecule that is isolated to conditions sufficient to cleave or excise said at least one cleavable or excisable base of said oligonucleotide, thereby dissociating said polynucleotide molecule of said library from said capturing molecule.

14. The method of claim 13, wherein said polynucleotide molecule of said library is pre-bound to an enrichment solid support.

15. The method of claim 1, wherein said polynucleotide adapters are DNA, RNA, or a mixture of DNA and RNA.

16. The method of claim 1, wherein said first strand further comprises a single base 3' overhang.

17. The method of claim 1, wherein a first nucleotide at a 5'-end of said first strand, said second strand, or both lacks a free phosphate group.

18. The method of claim 1, wherein said first strand region of complementarity comprises a barcode sequence or a portion thereof.

19. The method of claim 1, wherein said plurality of cleavable or excisable bases are selected from the group consisting of a ribonucleic acid (RNA) base, a uracil base, an inosine base, 2,6-diamino-4-hydroxy-5-formamidopyrimidine (FapyG) base, 8-oxo-7,8-dihydroguanine (8oxoG) base, and a photocleavable base.

20. The method of claim 1, wherein a first cleavable or excisable base of said plurality of cleavable or excisable bases is within 10 nucleotides to a second cleavable or excisable base of said plurality of cleavable or excisable bases.

* * * * *